(12) United States Patent
Zain-Luqman et al.

(10) Patent No.: US 11,268,093 B2
(45) Date of Patent: Mar. 8, 2022

(54) THERAPEUTIC METHOD FOR HUNTINGTON'S DISEASE

(71) Applicants: Rula Zain-Luqman, Taby (SE); C. I. Edvard Smith, Stockholm (SE)

(72) Inventors: Rula Zain-Luqman, Taby (SE); C. I. Edvard Smith, Stockholm (SE); Eman Zaghloul, Huddinge (SE); Pedro Moreno, Maia (PT); Olof Gissberg, Hagersten (SE); Karin Lundin, Malmkoping (SE); Jesper Wengel, Langeskov (DK); Liam Good, London (GB); Helen Bergquist, Kista (SE)

(73) Assignees: Rula Zain-Luqman, Taby (SE); C. I. Edvard Smith, Stockholm (SE)

( * ) Notice: Subject to any disclaimer, the term of this patent is extended or adjusted under 35 U.S.C. 154(b) by 133 days.

(21) Appl. No.: 16/475,642

(22) PCT Filed: Dec. 29, 2017

(86) PCT No.: PCT/EP2017/084839
§ 371 (c)(1),
(2) Date: Jul. 2, 2019

(87) PCT Pub. No.: WO2018/127462
PCT Pub. Date: Jul. 12, 2018

(65) Prior Publication Data
US 2021/0024922 A1  Jan. 28, 2021

(30) Foreign Application Priority Data
Jan. 3, 2017  (SE) .................... 1750001-8

(51) Int. Cl.
C07H 21/04 (2006.01)
C12N 15/113 (2010.01)
A61P 25/28 (2006.01)
A61K 31/7088 (2006.01)
A61K 47/42 (2017.01)
C12Q 1/6883 (2018.01)

(52) U.S. Cl.
CPC ........ *C12N 15/113* (2013.01); *A61K 31/7088* (2013.01); *A61K 47/42* (2013.01); *A61P 25/28* (2018.01); *C12Q 1/6883* (2013.01); *C12N 2310/11* (2013.01); *C12Q 2600/156* (2013.01)

(58) Field of Classification Search
None
See application file for complete search history.

(56) References Cited

FOREIGN PATENT DOCUMENTS

| WO | 03013437 A2 | 2/2003 |
| WO | 2011097641 A1 | 8/2011 |
| WO | 2012144906 A1 | 10/2012 |
| WO | 2013130824 A1 | 9/2013 |
| WO | 2013138662 A1 | 9/2013 |

OTHER PUBLICATIONS

Southwell et al. ("In vivo evaluation of candidate allele-specific mutant huntingtin gene silencing antisense oligonucleotides." Molecular Therapy 22.12 (2014): 2093-2106).*
Saini, Natalie, et al. "When secondary comes first-the importance of non-canonical DNA structures." Biochimie 95.2 (2013): 117-123.*
Johannsen, Marie W., et al. "Amino acids attached to 2'-amino-LNA: synthesis and excellent duplex stability." Organic & biomolecular chemistry 9.1 (2011): 243-252.*
Bergquist, Helen, et al. "Disruption of higher order DNA structures in Friedrich's ataxia (GAA) n repeats by PNA or LMA targeting." PLoS One 11.11 (2016): e0165788.*
Persichetti et al., Differential expression of normal and mutant Huntington's disease gene alleles, Neurobiol Dis, 1996, p. 183-190, vol. 3.
Lu et al., A novel human embryonic stem cell-derived Huntington's disease neuronal model exhibits mutant Huntington (mHTT) aggregates and soluble mHTT-dependent neurodegeneration, FASEB J, 2013, p. 1820-1829, vol. 27.
Banez-Coronel, M.et al. (2012) A Pathogenic Mechanism in Huntington's Disease Involves Small CAG-Repeated RNAs with Neurotoxic Activity. Plos Genet, 8(2)).
Wojtkowiak-Szlachcic, A. (2015) Short antisense-locked nucleic acids (all-LNAs) correct alternative splicing abnormalities in myotonic dystrophy. vol 43, p. 3318-3331 Nucleic Acids Research.
Ezzat K. et al. 2011. Pepfect 14 a novel cell-penetrating peptide for oligonucleotide delivery in solution and solid formulation. vol. 39, p. 5284-5298 Nucleic Acids Research.
Rué L. et al. 2016. Targeting CAG repeat RNAs reduces Huntington's disease phenotype independently of Huntington levels. vol. 126, p. 4319-4330. The Journal of Clinical Investigations; abstract.
Hu J. et al. 2009. Cellular localization and allele-selective inhibition of mutant huntingtin protein by peptide nucleic acid oligomers containing the fluorescent nuceobase. Bioorganic & Medicinal Chemistry Letters, vol. 19, No. 21, p. 6181-6184, Amsterdam.
Zaghloul E.M. et al. 2011. Optimizing anti-gene oligonucleotide Zorro-LNA for improved strand invasion into duplex DNA. vol. 39, No. 3, p. 1142-1154. Nucleic Acids Research.

(Continued)

*Primary Examiner* — Kimberly Chong
(74) *Attorney, Agent, or Firm* — Kim IP Law Group LLC

(57) ABSTRACT

The present invention relates to anti-gene oligonucleotides adapted to hybridize to DNA in a HTT gene, which are based on locked nucleic acids, phosphorodiamidate morpholino oligomers, (PMO) or equivalent oligonucleotide analogues comprising a $(CAG)_n$ sequence, and whose target is a sequence where the majority of the repeats are CAG/CTG, for use in down regulating the expression of the HTT gene, resulting in reduced HTT mRNA and protein levels in afflicted subjects, or in diagnosis, treatment and/or prevention of Huntington's disease, and where the anti-gene oligonucleotides target non-canonical DNA structures, including hairpin and cruciform. The invention also relates to a delivery system comprising said oligonucleotides and said use thereof.

19 Claims, 11 Drawing Sheets

Specification includes a Sequence Listing.

(56) References Cited

OTHER PUBLICATIONS

Sun, Xin et al. 2014. Phosphorodiamidate morpholino oligomers suppress mutant huntingtin expression and attenuate neurotoxicity. vol. 23, No. 23, p. 6302-6317 Human Molecular Genetics.

Gagnon, Keith T. et al. 2010. Allele-Selective Inhibition of Mutant Huntingtin Expression with Antisense Oligonucleotides Targeting the Expanded CAG Repeat. vol. 49, No. 47, p. 10166-10178. Biochemistry.

Sadri-Vakili et al. 2006. Histone deacetylase inhibitors: a novel therapeutic approach to Huntingtons's disease (complex mechanism of neuronal death). vol. 3, No. 4, p. 403-408. Current Alzheimer Rese, Bentham Science Publ. Ltd, NL.

Wang et al., 2006, Non-B DNA structure-induced genetic instability, Mutat. Res., 598, p. 103-119.

Written Opinion in International Application No. PCT/EP2017/084839, dated Apr. 12, 2018.

International Search Report in International Application No. PCT/EP2017/084839, dated Apr. 12, 2018.

\* cited by examiner

Fig. 1
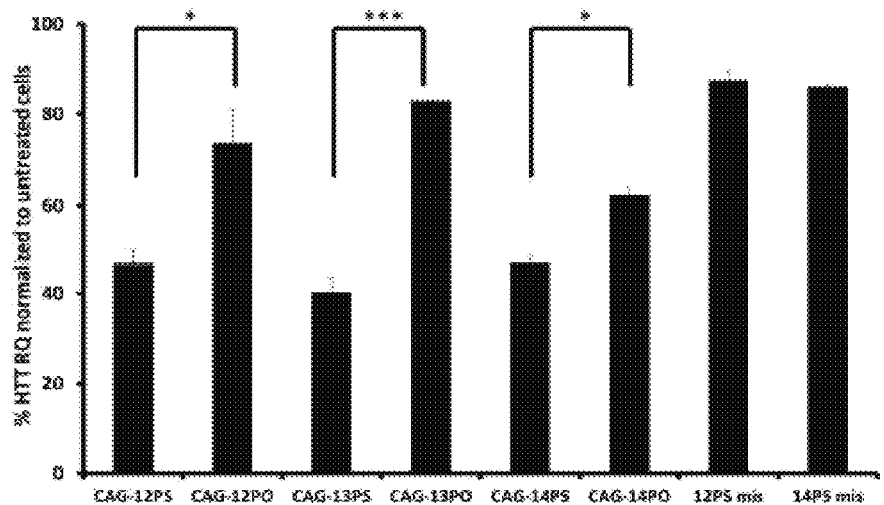
(a)
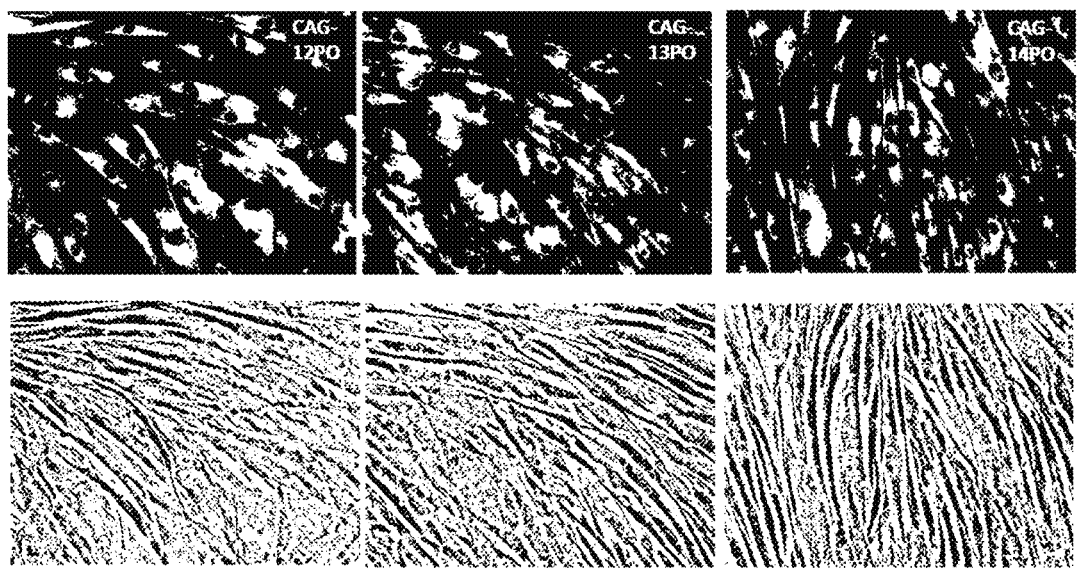
Fig. 1(b)

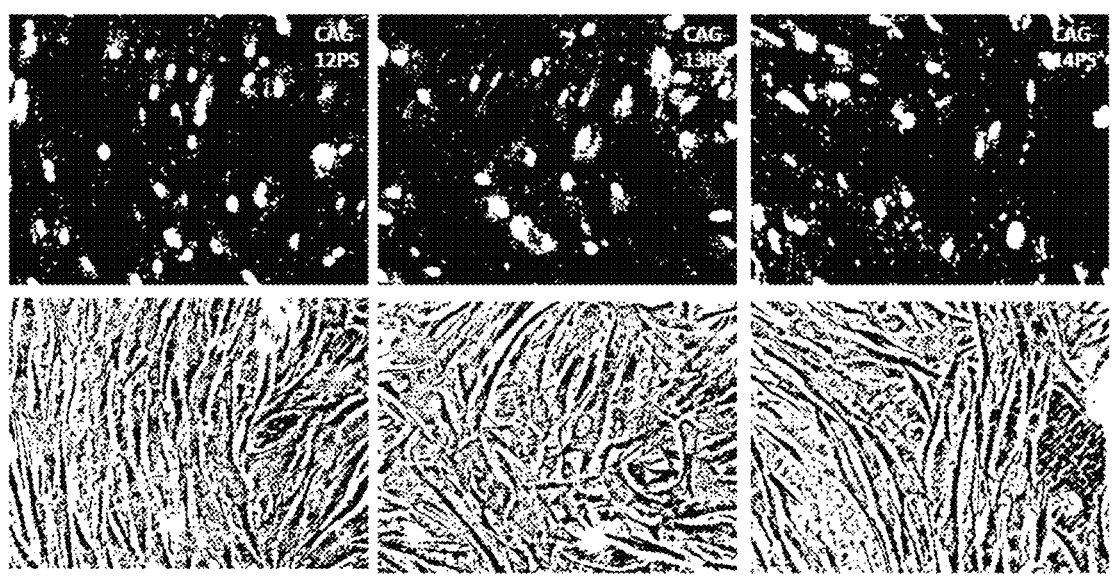
Fig. 1 (b) (cont.)

Fig. 9
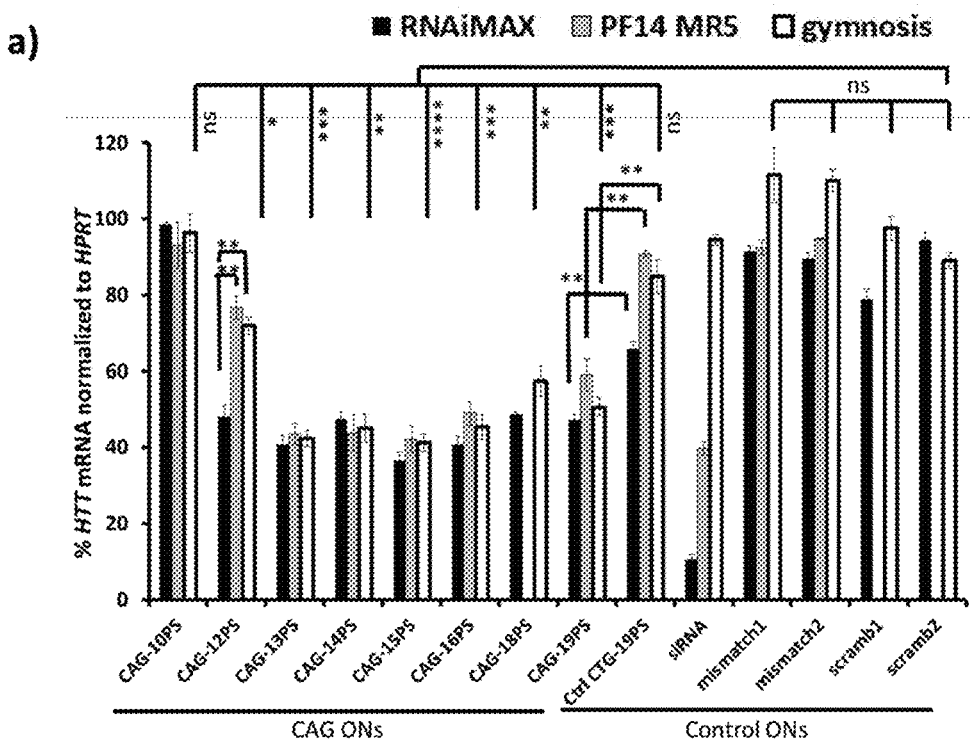
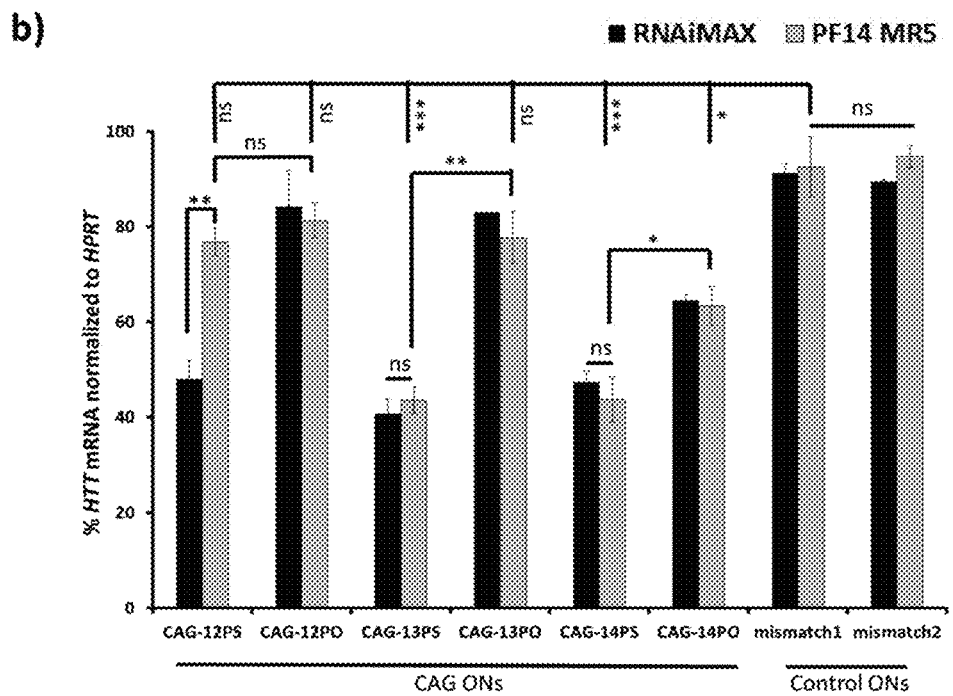

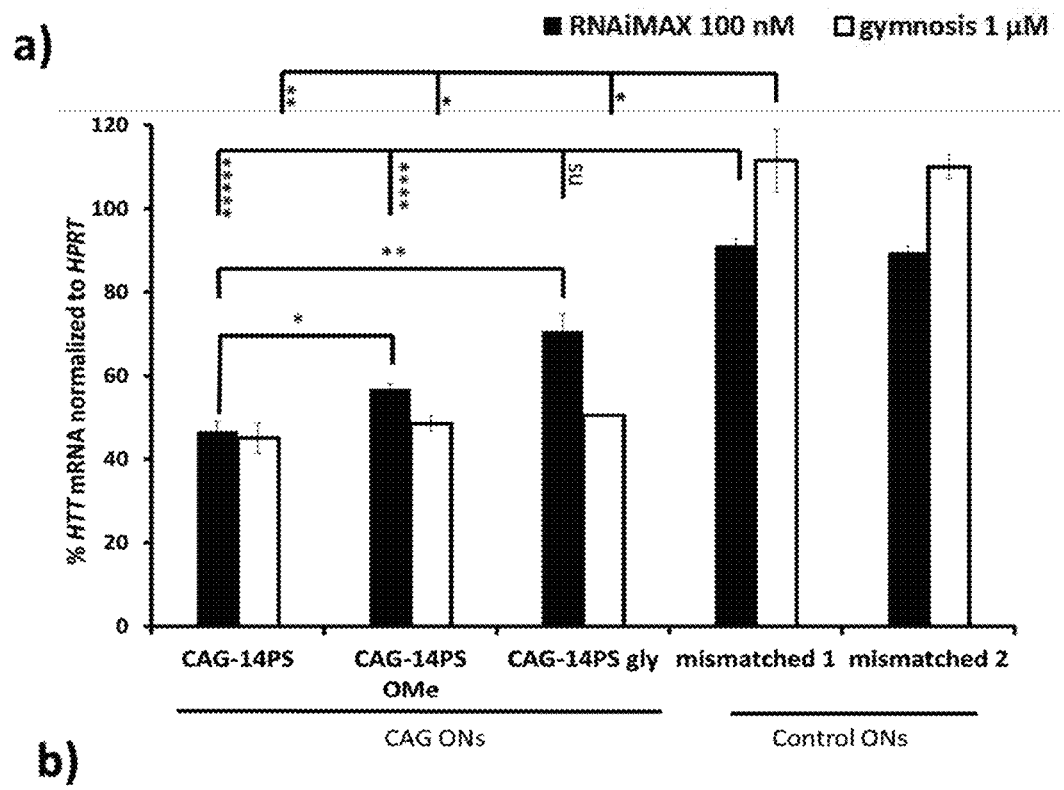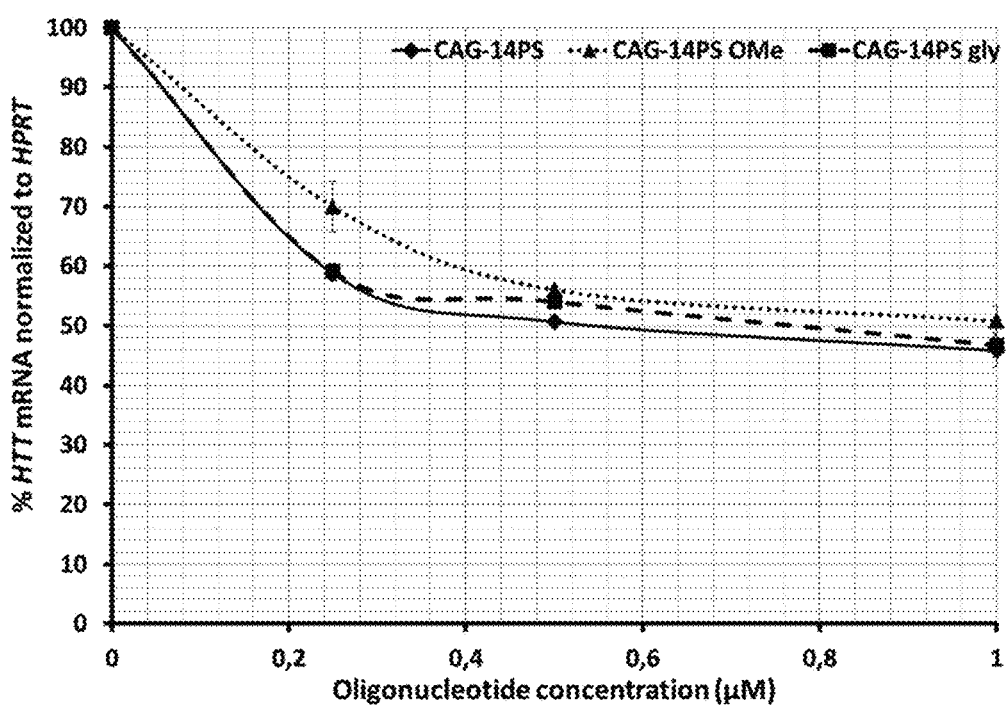
Fig. 10

THERAPEUTIC METHOD FOR HUNTINGTON'S DISEASE

CROSS-REFERENCE TO RELATED APPLICATIONS

This application is a U.S. national phase application under 35 U.S.C. § 371 of International Application No. PCT/EP2017/084839 filed on Dec. 29, 2017, which claims priority to Swedish Patent Application No. 1750001-8, filed Jan. 3, 2017, the entire disclosure of each of the applications are hereby incorporated by reference in their entirety for all purposes.

SEQUENCE LISTING

The instant application contains a Sequence Listing which has been filed electronically in ASCII format and is hereby incorporated by reference in its entirety. Said ASCII copy, created on Aug. 14, 2019, is named 1052_0028-28US_SL.txt and is 19,321 bytes in size.

TECHNICAL FIELD

The present invention relates to anti-gene oligonucleotides adapted to hybridize to DNA in an HTT gene, which are based on locked nucleic acids (LNA), phosphorodiamidate morpholino oligomers (PMO), or equivalent oligonucleotide analogues comprising a $(CAG)_n$ sequence, and whose target is a sequence where the majority of the repeats are CAG/CTG with CAG on one strand and CTG, running in the opposite orientation on the opposite strand, for use in down regulating the expression of the HTT gene resulting in reduced HTT mRNA and protein levels in afflicted subjects, or in diagnosis, treatment and/or prevention of Huntington's disease, and where the anti-gene oligonucleotides target non-canonical DNA structures, including hairpin and cruciform. The invention also relates to a delivery system comprising said oligonucleotides and said use thereof.

BACKGROUND OF THE INVENTION

Huntington's disease (HD) is a fatal, neurodegenerative disorder affecting the striatum, cerebral cortex and other subcortical structures. HD onset appears around midlife in most cases, and is characterized by a combination of symptoms: movement abnormalities, emotional disturbances and cognitive impairments. The most characteristic feature in HD patients is the uncoordinated irregular movements. However, this is usually preceded by a number of psychiatric symptoms and cognitive difficulties. In most cases, HD symptoms begin at 35-50 years of age and end with death 15-20 years later. Despite the identification of the genetic cause of HD in 1993, no approved therapy has yet been developed. Current pharmaceuticals can only provide symptomatic amelioration but fail to treat the underlying cause or stop disease progression.

HD is caused by a polyglutamine (polyQ)-encoding CAG/CTG repeat expansion in exon 1 of the Huntingtin (HTT) gene leading to the formation of mutant HTT (muHTT) protein. The length of the repeats in the mutant allele inversely correlates with the age of onset. The prevalence of HD is one of the highest among the monogenic neurological disorders in the developed world affecting 10-12 in 100,000 individuals. In HD there is a gain-of-function of the muHTT protein, while the loss of wild-type HTT (wtHTT), to certain extent, was proven to be safe [(Persichetti, F., Carlee, L., Faber, P. W., McNeil, S. M., Ambrose, C. M., Srinidhi, J., Anderson, M., Barnes, G. T., Gusella, J. F. and MacDonald, M. E. (1996) Differential expression of normal and mutant Huntington's disease gene alleles. Neurobiol Dis, 3, 183-190)]. Complete loss of wtHTT during embryonic development was found to be lethal, while decreasing wtHTT levels in adult animals seems to be well tolerated. Encouragingly, in a human embryonic stem cell-derived neuronal model, a 10-20% reduction of the muHTT alone was sufficient to show significant reduction of toxicity, whereas reducing wtHTT by up to 90% was described as safe [(Lu, B. and Palacino, J. (2013) A novel human embryonic stem cell-derived Huntington's disease neuronal model exhibits mHTT aggregates and soluble mHTT-dependent neurodegeneration. FASEB J, 27, 1820-1829)]. In addition, studies in Rhesus monkeys showed that a 45% reduction in the putamen resulted in no mobility or neurotoxic effects during the 6 weeks follow up [(McBride, J. L., Pitzer, M. R., Boudreau, R. L., Dufour, B., Hobbs, T., Ojeda, S. R. and Davidson, B. L. (2011) Preclinical Safety of RNAi-Mediated HTT Suppression in the Rhesus Macaque as a Potential Therapy for Huntington's Disease. Molecular Therapy, 19, 2152-2162)]. Interestingly, humans with a heterozygous translocation interrupting the HTT gene and who have reduced levels of HTT displayed no phenotypic abnormality. Altogether, lowering muHTT at the expense of a partial loss of wtHTT may be acceptable in a clinical context for adult patients. There is some evidence that HTT transcripts also contribute to HD toxicity [(Banez-Coronel, M., Porta, S., Kagerbauer, B., Mateu-Huertas, E., Pantano, L., Ferrer, I., Guzman, M., Estivill, X. and Marti, E. (2012) A pathogenic mechanism in Huntington's Disease involves small CAG-repeated RNAs with neurotoxic activity. Plos Genet, 8(2)); Rué L, Bañez-Coronel M, Creus-Muncunill J, Giralt A, Alcalá-Vida R, Mentxaka G, Kagerbauer B, Zomeño-Abellán M T, Aranda Z, Venturi V, Pérez-Navarro E, Estivill X, Marti E. Targeting CAG repeat RNAs reduces Huntington's disease phenotype independently of huntingtin levels. J Clin Invest. 2016 Nov. 1; 126(11):4319-4330.)]. RNA-related toxicity mechanisms have not been equally explored as those related to the muHTT protein, although both add to the overall pathogenic gain-of-function effect.

CAG-expanded HTT transcripts were shown to be retained in the nucleus of human HD fibroblasts and to co-localize with a splicing factor involved in the pathogenesis of CAG expanded transcripts. Moreover, the CAG repeat transcripts can be cleaved by Dicer resulting in aberrant generation of short repeated RNA. The latter was proven to cause inherent toxicity in a neuronal cell model, potentially contributing to the disease phenotype.

The monogenic origin of HD makes it an appealing target using oligonucleotides (ONs) that can affect the HTT gene expression. Different ON strategies, indeed, have been applied for targeting HTT, on the RNA level, such as siRNAs, splice-switching ONs, single nucleotide polymorphism (SNP)—targeting ONs, zinc finger nucleases and antisense ONs working via either RNase-mediated degradation or steric blocking of the HTT mRNA.

Previous trials for blocking HTT with ONs can be categorized according to their objective into two main classes, which both target RNA: allele-specific and non-allele specific strategies. Allele-specific silencing has been successfully achieved via antisense ONs that can bind to the HTT mRNA by steric blocking and prevent its translation. Such ONs, due to the difference in stability possessed by the mutant and wild-type RNA structures, could bind better to the muHTT mRNA. This approach was successfully achieved using antisense ONs with different chemistries, single-stranded RNAs and siRNAs with mismatches, which improved the mutant selectivity over the wild-type. However, ONs working by this strategy generally lack the advantage of decreasing the HTT mRNA levels, which were proven to add to the toxicity in HD. Alternatively, muHTT mRNA may include SNPs that can be targeted by gene silencing ONs to accomplish allele-specific HTT lowering. SNP targeting was first achieved using siRNAs, and then various antisense ONs with different chemical modifications have shown great success. This approach, however, cannot be generalized due to the SNP variability among HD patients; thus, prospective treatments need to be tailored to each group of individuals that carry the same mutation.

The non-allele specific approach has been recently suggested as a valid and safe option that would avoid the time-consuming and costly individualized therapy. Non-allele specific targeting of RNA has been achieved using antisense ONs targeting outside the CAG repeat region and inducing degradation of HIT mRNA via RNase H recruitment. Furthermore, a number of siRNAs have been developed to degrade the HIT mRNA via an RNA interference process. It is well known that the cleavage of target mRNA induced by siRNAs occurs in a catalytic and fast manner, which might result in undesirable drastic decrease in wtHTT protein levels. In general, degrading mRNA in case of HD might not be the best treatment option since the production of small CAG-repeated RNAs has been shown to cause neurotoxicity. Both polyQ-expanded HTT protein and the corresponding transcript are neurotoxic. A direct therapeutic approach would be to target the genomic HTT DNA.

An example of approaches targeting RNA is WO2011097641, which discloses use of ONs for treatment in repeat expansion diseases by targeting the repeat region within RNA.

WO 2013138662 and Wojtkowiak-Szlachcic, et al, Nucleic Acids Research, Vol 43, p 3318-3331, 2015, also discloses use of ONs for targeting RNA for the down regulation of DMPK.

WO2012144906 discloses use of ONs for targeting RNA for the down regulation of DMPK, SCA8 and JPH3.

SUMMARY OF THE INVENTION

The invention is based on a method using ONs with the capacity to bind to the HTT gene, i.e. to hybridize through hydrogen bonds, such as Watson-Crick (W-C) base-pairing to this region of the genomic DNA and with the capacity to reduce the expression of mRNA, and, as a consequence of the reduced mRNA HTT levels, also reduce HTT protein. W-C base-pairing to a single-stranded cognate target sequence is very straightforward and forms the basis for numerous applications in the biomedicine and biotechnology sector. However, W-C base-pairing to a double-stranded target, such as genomic DNA, is severely hampered by the existing base-pairing of the two anti-parallel cognate strands. While naturally occurring DNA breathing constantly results in short term loss of W-C base-pairing, the nature of this loss is such that strand-invasion and hybridization to an added cognate single-stranded ON is an extremely rare phenomenon. Given the existing W-C hybridization between the two strands in the helix, the added single-stranded ON must have the capacity to overcome this hurdle, i.e. the added single-stranded ON must outperform the natural hybridization. For this to occur, the added ON must perform better, i.e. must show a stronger hybridization. Over the last decades new chemistries have been developed, yielding enhanced hybridizing properties of such ONs. Examples of such chemistries are peptide nucleic acid (PNA) and locked nucleic acid (LNA). However, under physiological conditions they behave rather poorly when targeting double-stranded DNA.

CAG/CTG repeats form alternative DNA structures that are collectively called non-B DNA (G Wang and Vasquez K M. (2006). Non-B DNA structure-induced genetic instability. Mutat Res 598: 103-119). Due to intrastrand self-interactions, the CAG/CTG region has been shown to form hairpin and cruciform structures. These have been suggested to form during replication, transcription and repair, where single strands are frequently exposed. It is generally believed that during such events, the bulk majority of the CAG/CTG expansions occur due to mechanisms disrupting normal processing. Longer CAG/CTG repeat stretches have higher propensity to shift into the hairpin non-B-DNA form.

Down regulation of HTT mRNA and protein without involvement of RNA degradation, while keeping the wtHTT to the acceptable safe thresholds, seems an attractive therapeutic option for Huntington's disease (HD). Oligonucleotides (ONs) that can directly bind to the HTT gene and block its transcription may be useful for this purpose, because interfering at the gene level may provide a partial, but potentially long-term down regulation, which in turn will decrease the dosing frequency. This will also reduce the cost for health care.

The objective of the invention is achieved by anti-gene ONs comprising a $(CAG)_n$ sequence and which are based on locked nucleic acids (LNA), phosphorodiamidate morpholino oligomers (PMO) or equivalent ON analogues, wherein n is between 3 and 200 (SEQ ID NO: 45). In one embodiment, the ON is based on locked nucleic acids (LNA).

In one embodiment, the one or more anti-gene oligonucleotides, adapted to hybridize to DNA in an HTT gene, which are based on locked nucleic acids, phosphorodiamidate morpholino oligomers (PMO) or equivalent oligonucleotide analogues comprising a $(CAG)_n$ sequence, and whose target is a sequence where the majority of the repeats are CAG/CTG, and where the first complete repeat is optionally preceded by a G/G or an AG/TG, and/or where the last repeat is optionally followed by a C/C or a CA/CT, wherein n is between 3 and 200 (SEQ ID NO: 46), for use in treatment and/or prevention of Huntington's disease, and where the anti-gene oligonucleotides target non-canonical DNA structures, including hairpin and cruciform.

In another embodiment, the one or more anti-gene oligonucleotides, adapted to hybridize to DNA in an HTT gene, which are based on locked nucleic acids, phosphorodiamidate morpholino oligomers (PMO), or equivalent oligonucleotide analogues comprising a $(CAG)_n$ sequence, and whose target is a sequence where the majority of the repeats are CAG/CTG, and where the first complete repeat is preceded by a G/G or an AG/TG, and/or where the last repeat is followed by a C/C or a CA/CT, wherein n is between 3 and 200 (SEQ ID NO: 46), for use in treatment and/or prevention of Huntington's disease, and where the anti-gene oligonucleotides target non-canonical DNA structures, including hairpin and cruciform.

The resulting intrastrand self-interactions of the CAG/CTG repeat region have been shown by the inventors to constitute a unique and accessible target for the CAG-ONs to bind in the genomic context of the HTT locus. Multiple ONs can bind head-to-tail and disrupt the hairpin structures providing stable hybridization with the transcribed (CTG) DNA strand resulting in reduced production of HTT mRNA and protein.

In one embodiment, the one or more ONs comprise a phosphodiester (PO) or a phosphorothioate (PS) backbone. In another embodiment, the one or more ONs comprise or consist of a phosphodiester (PO) or a phosphorothioate (PS) backbone and which are based on LNA, phosphorodiamidate morpholino oligomers (PMO), lipid-modified forms of LNA or related ON analogues, such as 2',4'-constrained ONs, such as ethyl bicyclic nucleic acids, or ONs with modifications in their 2' or 5 positions, such as 2'-O-methyl, 2'-aminoglycyl (gly), piperazine-modified 2'-aminonucleotides, aminated 2'-amino-LNA nucleotides and 5-propargylamino-LNA.

In one embodiment, the one or more ONs comprise or consist of 2'-O-methyl RNA/LNA, such as CAG-14PS-OMe, i.e. a 14-mer oligonucleotide with phosphorothioate linkages targeting the CTG repeat, or 2'-glycylamino 5-methylcytosine LNA, such as CAG-14PS-gly. Exemplary sequences are disclosed as SEQ ID NOS:1-5.

In one embodiment, the one or more ONs are based on locked nucleic acids, phosphorodiamidate morpholino oligomers or related oligonucleotide analogues selected from the group comprising 2',4'-constrained oligonucleotides and oligonucleotides with modifications in their 2' or 5 positions.

In another embodiment, the one or more ONs are selected from the group comprising ethyl bicyclic nucleic acids, 2'-O-methyl, 2'-aminoglycyl, piperazino-modified 2'-aminonucleotides and 5-propargylamino-LNA, aminated 2'-amino-LNA nucleotides, lipid-modified forms of LNA, and phosphorodiamidate morpholino oligomers (PMO). In a further embodiment, the one or more ONs are selected from the group comprising 2'-O-methyl RNA/LNA, and 2'-glycylamino 5-methylcytosine LNA.

In one embodiment, the one or more ONs are selected from the group comprising CAG-14PS-OMe (2'-O-methyl) and CAG-14PS-gly (2'-aminoglycyl).

In yet another embodiment, the one or more ONs are based on 2'-aminoglycyl modified nucleotide, such as modified A, G, C or T.

In another embodiment, one or more ONs are based on phosphorodiamidate morpholino oligomers (PMOs).

The one or more ONs have the ability to invade double strand DNA and bind to one of the strands forming the DNA duplex structure.

In one embodiment, the one or more ONs are selected from the group comprising or containing CAG-10PS, CAG-12PS and CAG-12PO, CAG-13PS and CAG-13PO, CAG-14PS and CAG-14PO, CAG-14PS-OMe, CAG-14PS-gly, CAG-15PS, CAG-16PS, CAG-18PS and CAG-19PS. In another embodiment, the one or more ONs are selected from the group comprising or containing CAG-10PS, CAG-12PS, CAG-13PS, CAG-14PS, CAG-14PS-OMe, CAG-14PS-gly, CAG-15PS, CAG-16PS, CAG-18PS and CAG-19PS. In yet another embodiment, the one or more ONs are selected from the group comprising or containing CAG-12PS, CAG-13PS, CAG-14PS, CAG-15PS, CAG-16PS, CAG-18PS and CAG-19PS. In a further embodiment, the one or more ONs are selected from the group comprising or containing CAG-14PS, CAG-15PS, CAG-16PS, CAG-18PS and CAG-19PS. In one embodiment, the ON is CAG-14PS, CAG-14PS-OMe, CAG-14PS-gly. In another embodiment, the ON is CAG-15PS. In yet another embodiment, the ON is CAG-15PS-OMe, CAG-15PS-gly. In one embodiment, the ON is CAG-16PS. In another embodiment, the ON is CAG-18PS. In one embodiment, the ON is CAG-19PS. In yet a further embodiment relates to mixtures of two or more of any one of the ONs mentioned above.

The invention relates to one or more ONs as defined above for use in therapy.

Another embodiment relates to one or more anti-gene ONs as defined above for use in down regulating the expression of an HTT gene. One embodiment relates to one or more anti-gene ONs as defined above for use in down regulating HTT mRNA and protein levels in afflicted subjects. One embodiment relates to one or more anti-gene ONs as defined above for use in targeting non-canonical DNA structures at the CAG/CTG repeat sequence, including hairpin and cruciform.

A further embodiment relates to one or more anti-gene ONs as defined above for use in treatment and/or prevention of HD. Prevention may also relate to blocking the expansion of the CAG/CTG repeats. In an embodiment, the one or more anti-gene oligonucleotides as defined above are for use in prevention of Huntington's disease, where prevention is related to blocking the CAG/CTG repeat expansion.

One embodiment relates to one or more anti-gene ONs as defined above for use in down regulating the expression of an HTT gene and for use in down regulating HTT mRNA and protein levels or for use in targeting non-canonical DNA structures at the CAG/CTG repeat sequence, including hairpin and cruciform, in fibroblasts or in fibroblasts from HD patients, such as GM04281, in vivo.

Another embodiment relates to one or more anti-gene ONs as defined above for use in down regulating HTT mRNA and/or protein levels in afflicted subjects or in said fibroblasts, whereby HTT mRNA and/or protein levels are down regulated for at least up to 10 days.

Another embodiment relates to a method of treating, preventing or reducing the risk of a disease, disorder or condition in which down regulating the expression of an HTT gene, or down regulating HTT mRNA and protein levels in afflicted subjects, or treatment and/or prevention of HD is beneficial, which comprises administering to a mammal, such as a human, in need thereof, a therapeutically effective amount of one or more anti-gene ONs as defined above.

The ONs as mixmers of DNA, RNA or nucleic acids analogues, and locked nucleic acid (LNA) nucleotides have a capacity of strand-invasion into double-stranded DNA (dsDNA), thereby binding to the HTT gene template strand. The ONs of the invention allow for a sequence specific targeting of chromosomal dsDNA. Therefore, the ONs cause down regulation of HTT mRNA and protein levels in HD patients as well as in patient cell lines.

In contrast to prior art, the unique treatment approach of the invention is to target the DNA corresponding to the repeat region in the gene. The ONs are independent of any antisense mechanism of action (such as RNase H or RNAi). In fact, evidence shows that the ONs of the invention only bind to DNA and not to HTT RNA (see FIGS. 6 and 7). In addition, the effect of the ONs comes from the unique invasion of secondary structures known as "hairpins" and "cruciform" formed at the repeat regions in the DNA. The ONs have an effect by binding directly to DNA, interfering with transcription, rather than with the downstream effect associated with antisense technologies (see FIG. 8)

One embodiment relates to the use of any one or more oligonucleotides adapted to hybridize to DNA in an HTT gene, which are based on locked nucleic acids, phosphorodiamidate morpholino oligomers (PMO) or equivalent oligonucleotide analogues comprising a $(CAG)_n$ sequence, and whose target is a sequence where the majority of the repeats are CAG/CTG, and where the first complete repeat is optionally preceded by a G/G or an AG/TG, and/or where the last repeat is optionally followed by a C/C or a CA/CT, wherein n is between 3 and 200 (SEQ ID NO: 46), as defined above, in down regulating the expression of the HTT gene, or for targeting non-canonical DNA structures at the CAG/CTG repeat sequence, including hairpin and cruciform, resulting in reduced HTT mRNA and protein levels in afflicted subjects, or in treatment and/or prevention of HD, and where the anti-gene oligonucleotides target non-canonical DNA structures, including hairpin and cruciform.

The invention also relates to the use of any one or more oligonucleotides adapted to hybridize to DNA in an HTT gene, which are based on locked nucleic acids, phosphorodiamidate morpholino oligomers (PMO) or equivalent oligonucleotide analogues comprising a $(CAG)_n$ sequence, and whose target is a sequence where the majority of the repeats are CAG/CTG, and where the first complete repeat is optionally preceded by a G/G or an AG/TG, and/or where the last repeat is optionally followed by a C/C or a CA/CT, wherein n is between 3 and 200 (SEQ ID NO: 46), as defined above, in the manufacture of a medicament for the treatment or prevention of a disease, disorder or condition in which down regulating the expression of an HTT gene, or for targeting non-canonical DNA structures at the CAG/CTG repeat sequence, including hairpin and cruciform, or down regulating HTT mRNA and protein levels in afflicted subjects, or treatment and/or prevention of HD, is beneficial, and where the anti-gene oligonucleotides target non-canonical DNA structures, including hairpin and cruciform. A further embodiment relates to any one or more oligonucleotides adapted to hybridize to DNA in an HTT gene which are based on locked nucleic acids, phosphorodiamidate morpholino oligomers (PMO) or equivalent oligonucleotide analogues comprising a $(CAG)_n$ sequence, and whose target is a sequence, where the majority of the repeats are CAG/CTG, and where the first complete repeat is optionally preceded by a G/G or an AG/TG, and/or where the last repeat is optionally followed by a C/C or a CA/CT, wherein n is between 3 and 200 (SEQ ID NO: 46), as defined above, in combination with other HD therapies, existing or future, such as siRNAs, splice-switching ONs, single nucleotide polymorphism (SNP) targeting ONs, zinc finger nucleases and antisense ONs working via either RNase-mediated degradation or steric blocking of the HTT mRNA, for use in down regulating the expression of the HTT gene, or in targeting non-canonical DNA structures at the CAG/CTG repeat sequence, including hairpin and cruciform, or in down regulating HTT mRNA and protein levels in afflicted subjects, or in treatment and/or prevention of Huntington's disease. A combination therapy may reduce toxicity and improve efficiency of the treatment.

In one embodiment, n is between 10 and 200, or between 10 and 150, or between 10 and 100, or between 10 and 125, or between 12 and 50, or between 12 and 30, or between 3 and 9, or between 12 and 20. In a further embodiment, n is between 12 and 15, or between 14 and 19. In yet another embodiment, n is 10, 11, 12, 13, 14, 15, 16 17, 18, 19 or 20. In one embodiment, n is 12, 13, 14, 15, 16, 18 or 19.

One embodiment relates to the use of any one or more of the anti-gene ONs defined above, without affecting other CAG sequences in other genes, i.e. without affecting non-HTT genes.

Another embodiment relates to the use of any one or more of the anti-gene ONs defined above, without binding to RNA.

The invention also relates to a delivery system for administration of any one or more oligonucleotides as defined above, comprising or consisting of
a) one or more of said oligonucleotides,
b) a liquid in which the one or more of oligonucleotides are dissolved, and optionally
c) a cell penetrating peptide/protein, such as PepFect 14 (PF14), or
d) a cationic lipid, or
e) a nuclear localization signal peptide, or
f) an aptamer facilitating targeting and uptake,
optionally together with a pharmaceutically acceptable carrier, adjuvant and/or excipient.

In one embodiment, the delivery system for administration of any one or more oligonucleotides as defined above, comprises or consisting of
a) one or more of said oligonucleotides,
b) a liquid in which the one or more of oligonucleotides are dissolved, and optionally
c) a cell penetrating peptide/protein, such as PepFect 14 (PF14),
optionally together with a pharmaceutically acceptable carrier, adjuvant and/or excipient.

In another embodiment, the one or more of oligonucleotides are selected from the group comprising or containing CAG-12PS, CAG-13PS, CAG-14PS, CAG-14PS-OMe, CAG-14PS-gly, CAG-15PS, CAG-16PS, CAG-18PS and CAG-19PS.

In a further embodiment, the delivery system for administration of any one or more oligonucleotides as defined above, comprises or consisting of
a) one or more of said oligonucleotides,
b) a liquid in which the one or more of oligonucleotides are dissolved, and
c) a cell penetrating peptide/protein, such as PepFect 14 (PF14),
optionally together with a pharmaceutically acceptable carrier, adjuvant and/or excipient, whereby the one or more of oligonucleotides comprise a phosphodiester (PO) backbone, such as ONs selected from the group comprising or containing CAG-12PO, CAG-13PO and CAG-14PO.

One embodiment, relates to any one of a delivery system as defined above, whereby a mixture of ingredients c), d), e) and/or f) is used.

The delivery system may improve efficiency of administration of the ON and thereby improve efficacy of therapy. The delivery system may also reduce toxicity.

The invention also relates to a combination of any one or more oligonucleotides adapted to hybridize to DNA in an HTT gene, which are based on locked nucleic acids, phosphorodiamidate morpholino oligomers (PMO) or equivalent oligonucleotide analogues comprising a $(CAG)_n$ sequence, and whose target is a sequence where the majority of the repeats are CAG/CTG, and where the first complete repeat is optionally preceded by a G/G or an AG/TG, and/or where the last repeat is optionally followed by a C/C or a CA/CT, wherein n is between 3 and 200 (SEQ ID NO: 46), as defined above, together with other HD therapies, such as siRNAs, splice-switching ONs, single nucleotide polymorphism (SNP) targeting ONs, zinc finger nucleases and antisense ONs working via either RNase-mediated degradation or steric blocking of the HTT mRNA. Examples of such combination may be one or more ONs selected from the group comprising or containing CAG-12PS, CAG-13PS, CAG-14PS, CAG-14PS-OMe, CAG-14PS-gly, CAG-15PS, CAG-16PS, CAG-18PS and CAG-19PS, and siRNAs, splice-switching ONs, single nucleotide polymorphism (SNP) targeting ONs, zinc finger nucleases and antisense ONs working via either RNase-mediated degradation or steric blocking of the HTT mRNA.

The invention further relates to a delivery system for administration of any one or more oligonucleotides as defined above, comprising or consisting of a) a combination of any one or more of the one or more of oligonucleotides defined above together with any other HD therapies, such as those mentioned above, b) a liquid in which the one or more of oligonucleotides are dissolved, and optionally c) a cell penetrating peptide/protein, such as PepFect 14 (PF14), or d) a cationic lipid or e) a nuclear localization signal peptide, or f) an aptamer facilitating targeting and uptake, optionally together with a pharmaceutically acceptable carrier, adjuvant and/or excipient.

One embodiment relates to the delivery system defined above, for use in down regulating the expression of a HTT gene, or in targeting non-canonical DNA structures at the CAG/CTG repeat sequence, including hairpin and cruciform, or for use in down regulating HTT mRNA and protein levels in afflicted subjects, or in diagnosis treatment and/or prevention of HD in afflicted subjects or subjects at risk of being afflicted.

The invention also relates to any one or more the oligonucleotides as defined above for use in diagnosis of HD.

One embodiment, relates to a method for diagnosis of HD, whereby the method comprises or contains the steps of 1) isolating genomic DNA from a biological sample, and optionally cleaving the isolated DNA, 2) adding any one or more of the anti-gene ONs defined above, and 3) determining length and sequence and/or number of CAG/CTG repeats in the HTT gene.

Cleaving may be done using DNA restriction enzymes, CRISPR-Cas9 based DNA cleavage or by fragmentation using ultra sonication.

The use of the ONs in diagnosis is based on the ONs ability to disrupt and bind the DNA hairpin and cruciform structures, thereby, allowing full reading of the DNA sequence, in analogy to binding the HTT gene for down regulating HTT mRNA and protein levels.

BRIEF DESCRIPTION OF DRAWINGS

FIG. 1. CAG PS ONs reach the nucleus and significantly down regulate HTT gene expression on mRNA level. LNA/DNA CAG 12-, 13- or 14-mer ONs, with either PS or PO backbone, were transfected at 100 nM concentration after formulation with the commercial cationic lipid RNAiMAX into human HD patient fibroblasts GM04281. Four days post treatment, the cells were lysed and RNA was isolated and further analysed by q RT-PCR. (a): shows the HTT mRNA levels after each treatment normalized to HPRT as a housekeeping reference gene. Significant differences were found between CAG-12PS versus CAG-12PO ($p<0.05$), CAG-13PS versus CAG-13PO ($p<0.0001$), and CAG-14PS versus CAG-14PO ($p<0.01$). Mismatched ON1 and mismatched ON2 are used as control ONs and are significantly different from all constructs except for the 13PO and 14PO (significance levels shown in the figure). (b): shows the uptake behaviour of Cy5 labelled ONs (PS or PO backbone) after transfection into GM04281 fibroblasts as detected by fluorescence microscopy of live cells.

FIG. 9. CAG ONs can be delivered to the patient fibroblasts by peptide and gymnotic delivery. (a): LNA/DNA CAG 10- to 19-mer PS ONs were transfected at 100 nM into GM04281 human HD fibroblasts using RNAiMAX or PepFect 14 (PF14) at molar ratio 1:5 (ON: peptide) or were added to the cells at 1 μM without transfection reagents (gymnosis). Control CTG-19PS, mismatched, scrambled ONs and siRNA were used as controls. Four days post treatments, the cells were lysed and RNA was isolated and analyzed by q RT-PCR using primers and probes for HTT and HPRT as a housekeeping reference gene. Significant differences were found between CAG-19PS and CTG-19PS using all delivery methods (RNAiMAX (p<0.01), PF14 (p<0.01), gymnosis (p<0.0001)). All ONs ranged from 12 to 19-mer delivered by gymnosis significantly reduced HTT mRNA (significance levels are shown in the graph). (b): LNA/DNA CAG 12-, 13- or 14-mer ONs with either PS or PO backbone were transfected at 100 nM concentration after formulation with RNAiMAX or with PF14 at molar ratio 1:5 (ON: peptide) into human HD patient fibroblasts GM04281. There was no significant (ns) difference between RNAiMAX and PF14 formulations with CAG-13PS and CAG-14PS. For PF14 formulations, the mismatched controls differed significantly from all treatments except for CAG-12PS, CAG-12PO and CAG-13PO (significance levels for all ONs compared to mismatched 1 are shown in the figure).

FIG. 10. Effect of ON chemical modifications on efficiency. (a): CAG-14PS, CAG-14PS-OMe and CAG-14PS-gly were transfected at 100 nM into GM04281 human HD fibroblasts using RNAiMAX, or were added to the cells at 1 μM concentration without transfection reagents (gymnosis). Four days post treatments, the cells were lysed and RNA was isolated and analysed by q RT-PCR using primers and probes for HTT and HPRT. Significant differences were found between mRNA levels after treatment with: CAG-14PS versus CAG-14PS-OMe (P<0.05), CAG-14PS versus CAG-14PS-gly (p<0.01). Significance levels of all ONs compared to mismatched 1 ON are shown in the figure. (b): a dose response curve for the three ONs after gymnosis with increasing concentrations of each ON in GM04281.

DETAILED DESCRIPTION OF INVENTION

Definitions

Figure 2:
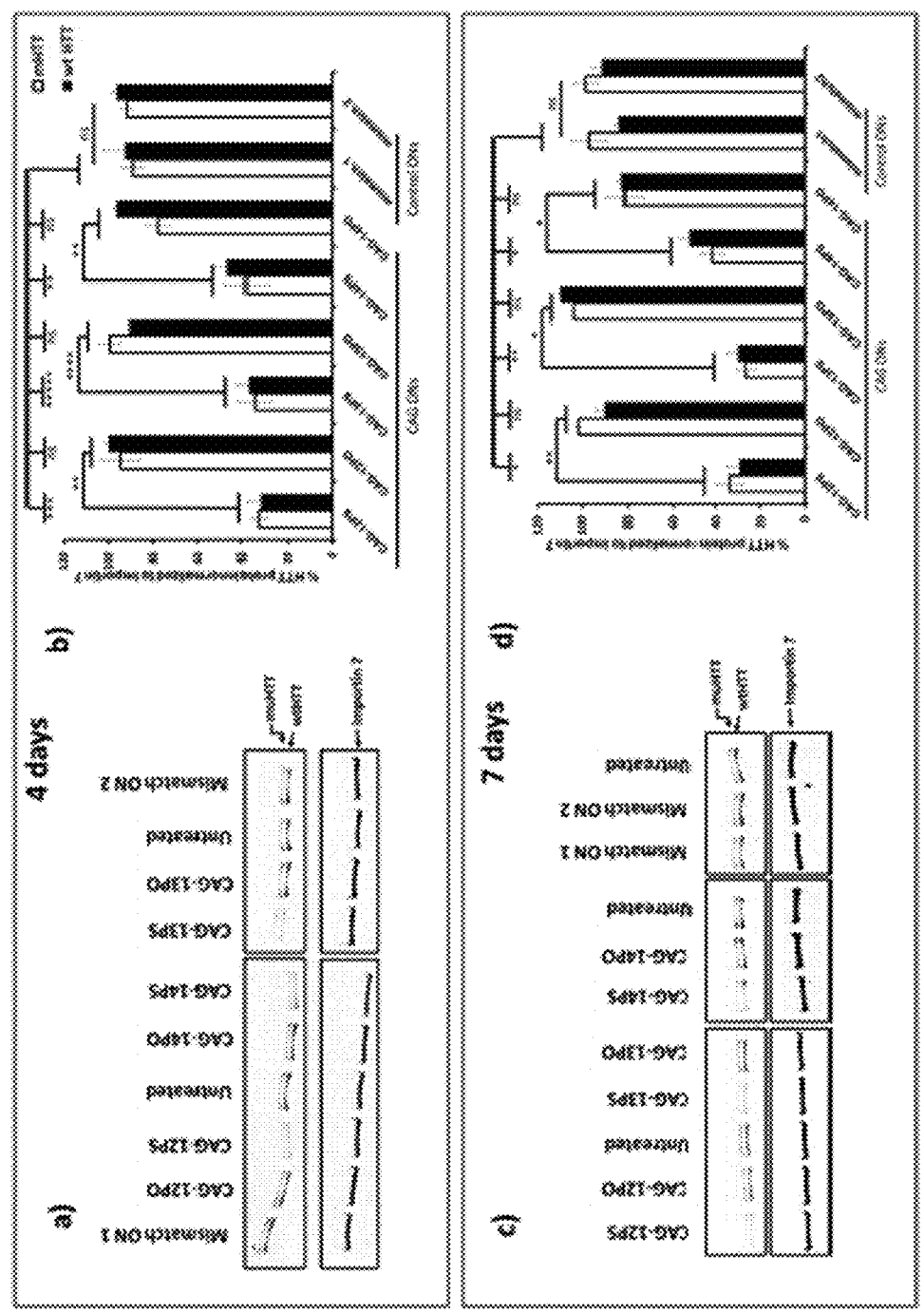
FIG. 2. CAG PS ONs significantly down regulate HTT gene expression on protein level. LNA/DNA CAG 12-, 13- or 14-mer ONs, with either PS or PO backbone, were transfected at 100 nM concentration after formulation with RNAiMAX into human HD patient fibroblasts GM04281. Four days (a) and (b) or seven days (c) and (d) post treatment, cells were lysed and western blots were performed to detect the HTT protein with its two isomers: muHTT and wtHTT. Importin 7 was used as a housekeeping control. (a) Shows a representative western blot gel for the 4 days-time point, while (c) shows a representative gel for 7 days. Results from three replicate experiments were quantified and plotted in (b) and (d) for the 4 and 7 days data respectively. There were significant differences between the total (mutant+wild-type) remaining HTT protein amounts after the treatment with: CAG-12PS versus CAG-12PO ($p<0.01$ and $p<0.01$, for 4 and 7 days), CAG-13PS versus CAG-13PO ($p<0.0001$ and $p<0.05$, for 4 and 7 days), CAG-14PS versus CAG-14PO ($p<0.01$ and $p<0.05$, for 4 and 7 days). Mismatched ON1 and ON2 were used as controls and there was no significant difference between them, whereas total HTT protein levels obtained by all PS ONs were significantly different from that obtained by mismatched ON1 (significance levels shown in the figure).

As used herein, the term "optional" or "optionally" means that the subsequently described event or circumstance may but need not occur, and that the description includes instances where the event or circumstance occurs and instances where it does not.

As used herein, "pharmaceutically acceptable" is employed herein to refer to those ONs, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In the context of the present specification, the term "therapy" also includes "prophylaxis" unless there are specific indications to the contrary. The term "therapeutic" and "therapeutically" should be construed accordingly. The term "therapy" within the context of the present invention further encompasses to administer an effective amount of one or more ONs of the present invention, to mitigate either a pre-existing disease state, acute or chronic, or a recurring condition. This definition also encompasses prophylactic therapies for prevention of recurring conditions and continued therapy for chronic disorders.

The oligonucleotides (ON)s defined herein and used in different aspects of this document are based on nucleotide analogues. By "based on" is meant that the ONs are built up by analogues of deoxyribo- or ribonucleotides including modifications of base, sugar and/or phosphodiester backbone. The ON analogues useful in the present context are disclosed in more detail elsewhere herein.

"Locked nucleic acid" (LNA) is an RNA analogue that synthesized as an ON has the ability to invade into double-stranded DNA structures. The ribose moiety of an LNA nucleotide is modified with an extra bridge connecting the 2' oxygen and 4' carbon.

The bridge "locks" the ribose in the 3'-endo (North) conformation, which is often found in the A-form duplexes. LNA nucleotides can be mixed with natural or modified DNA or RNA residues in the ON whenever desired. The locked ribose conformation enhances base stacking and backbone pre-organization. This significantly increases the hybridization properties (melting temperature) of ONs.

CAG/CTG repeat sequences refer to a double stranded DNA with a repeated CAG sequence on one strand and a complementary repeated CTG sequence on the other strand, such as in the mutated HTT gene. The number of CAG/CTG repeats in the human HTT gene may go up to more than 200 or 100 repeats. Such repeated DNA sequences are in the context of the present document called CAG/CTG repeat sequences.

A phosphorothioate modification includes substitution of one of the non-bridging oxygen atoms in a phosphodiester bond with sulphur. This chemical modification enhances the cell uptake of ONs as well as their resistance towards endogenous enzymatic cleavage. A hairpin structure is formed in one of the DNA strands carrying a self-complementary sequence, such as the repeat CAG/CTG sequence in the HTT gene.

A cruciform structure constitutes of two hairpin structures formed at each of the self-complementary DNA strands.

Regarding the wording " . . . and whose target is a sequence where the majority of the repeats are CAG/CTG, and where the first complete repeat is optionally preceded by a G/G or an AG/TG, and/or where the last repeat is optionally followed by a C/C or a CA/CT, . . . "

In the chromosome the coding strand of DNA, which has the same sequence as mRNA, contains one of the following repeats:

5'-$(CAG)_n$-3' (the repeat only consists of multiples of CAG),

G$(CAG)_n$C (the repeat consists of multiples of CAG, but with a 5' extension with G and/or 3' extension with C), AG$(CAG)_n$CA (the repeat consists of multiples of CAG, but with a 5' extension with AG and/or 3' extension with CA).

With the well-known antisense technology, the mRNA is targeted. Since the mRNA contains one of the above sequences, the corresponding antisense oligonucleotide consists of $(CTG)_n$, possibly with 5' and/or 3' extensions.

In the chromosome the template strand, which is copied to mRNA contains one of the following repeats:

5'-$(CTG)_n$-3' (the repeat only consists of multiples of CTG),

G$(CTG)_n$C (the repeat consists of multiples of CTG, but with a 5' extension with G and/or 3' extension with C), TG$(CTG)_n$CT (the repeat consists of multiples of CTG, but with a 5' extension of TG and/or 3' extension with CT).

With the anti-gene technology, the template strand of duplex DNA is uniquely targeted. Since the template strand contains one of the above sequences, the corresponding anti-gene oligonucleotide consists of $(CAG)_n$, possibly with 5' and/or 3' extensions.

The invention makes use of LNA-substituted oligonucleotides for their very good qualities in terms of hybridization. However, as mentioned, this is not sufficient for achieving strand-invasion into duplex DNA in a genomic context. Thus, the invention is based on the use of such single-stranded ONs and to direct them towards non-canonical DNA structures. In the HTT gene there are trinucleotide repeats, which are the origin of the toxicity. However, it is shown that these repeats form good targets for the LNA-based ONs. This is because such repeats form structures, whereby W-C hybridization between the two strands (interstrand hybridization) is interrupted and instead intrastrand hybridization is taking place generating the non-canonical conformation. Such sequences are, therefore, good targets for the synthetic ONs.

The anti-gene ONs comprise a $(CAG)_n$ sequence and are based on locked nucleic acids, phosphorodiamidate morpholino oligomers (PMO), or equivalent ON analogues, wherein n is between 3 and 200 (SEQ ID NO: 45). In one embodiment, n is between 3 and 30. In a further embodiment, n is between 3 and 10, or between 10 and 15, or between 14 and 19. Other examples of n may be 3, 4, 5, 6, 7, 8, 9 10, 1, 12, 13, 14, 15, 16 17, 18, 19, 20, 21, 22, 23, 24, 25, 26, 27, 28, 29 or 30.

A mixture of ONs may comprise ONs having the same or different lengths, for example a CAG-14 may be combined with CAG-14PS or CAG-19PS. Any possible combination of the ONs as defined above are included in the scope of the present invention. Equivalent nucleotide analogues may be other 2',4'-constrained nucleotides, such as ethyl bicyclic nucleic acids. Other related nucleotides are those with other modifications in their 2' or 5 positions, such as 2'-O-methyl, 2'-glycylamino, piperazino-modified 2'-aminonucleotides, aminated 2'-amino-LNA nucleotides, and 5-propargylamino-LNA. Thus, the ON may be modified and comprise 2'-O-methyl RNA/LNA, such as CAG-14PS-OMe or 2'-glycylamino 5-methylcytosine LNA, such as CAG-14PS-gly. Other examples are ONs based on 2'-aminoglycyl modified nucleotide, such as modified A, G, C or T, which also have the ability to invade double strand DNA and bind single strand DNA, thereby forming a duplex structure. In another embodiment, one or more ONs are based on phosphorodiamidate morpholino oligomers (PMO) or lipid-modified forms of LNA. The ONs may comprise a phosphodiester (PO) or a phosphorothioate (PS) backbone.

Examples of oligonucleotides are sequences 6-15 in Table 1. Included in the table are control sequences.

Table 1. ONs used in the study. CAG ONs are designed to target the template strand of the HTT gene, while CTG ONS are designed to target the mRNA and used here as controls. The CAG-12, -13 and -14 are made in two different versions, one with PO and the other with PS backbone. LNA bases are written in capital letters, while DNA in small. In the control siRNA, the RNA is written in small bold letters. In the ON CAG-14PS-OMe, the 2'-O-methyl RNA bases are superscripted with "m". In the ON CAG-14PS-gly, the 2'-glycylamino 5-methylcytosine LNA nucleotides are superscripted by "gly".

| ONs | Sequence | Sequence No. |
|---|---|---|
| CAG-10PS | 5'-cAgCAgCAgC | SEQ. ID NO: 6 |
| CAG-12PS and CAG-12PO | 5'-cAgCAgCAgCAg | SEQ. ID NO: 7 |
| CAG-13PS and CAG-13PO | 5'-cAgCAgCAgCAgc | SEQ. ID NO: 8 |
| CAG-14PS and CAG-14PO | 5'-cAgCAgCAgCAgCa | SEQ. ID NO: 9 |
| CAG-14PS-OMe | 5'-$^m$cA$^m$gCA$^m$gCA$^m$gCA$^m$gC$^m$a | SEQ. ID NO: 10 |
| CAG-14PS-gly | 5'-cAgC$^{gly}$AgC$^{gly}$AgC$^{gly}$AgC$^{gly}$a | SEQ. ID NO: 11 |
| CAG-15PS | 5'-cAgCAgCAgCAgCAg | SEQ. ID NO: 12 |
| CAG-16PS | 5'-cAgCAgCAgCAgCAgc | SEQ. ID NO: 13 |
| CAG-18PS | 5'-cAgCAgCAgCAgCAgCAg | SEQ. ID NO: 14 |
| CAG-19PS | 5'-cAgCAgCAgCAgCAgCAgc | SEQ. ID NO: 15 |

| Control ONs | Sequence | |
|---|---|---|
| Scramble ON1 (scramb.1) | 5'-gACgACgACgACgACgA | SEQ. ID NO: 16 |
| Scramble ON2 (scramb.2) | 5'-gAcGAcGAcGAcGAcGA | SEQ. ID NO: 17 |
| Mismatched ON1 (mismatch.1) | 5'-aAgAAgAAgAAg | SEQ. ID NO: 18 |
| Mismatched ON2 (mismatch.2) | 5'-aAgAAgAAgAAgAA | SEQ. ID NO: 19 |
| Mismatched ON3 (mismatch.3) | 5'-cAaCAgCAgCAaCAgCAa | SEQ. ID NO: 20 |
| Control CTG-13PS | 5'-cTgCTgCTgCTgc | SEQ. ID NO: 21 |
| Control CTG-13PS gap | 5'-gcTgcTcgTgcTg | SEQ. ID NO: 22 |
| Control CTG-19PS | 5'-gcTgcTgcTgcTgcTgcTg | SEQ. ID NO: 23 |
| SiRNA | 5'-cagacaaugauucacactttt uucuguuacuaagugugcc | SEQ. ID NOS: 24 and 53 |

The one or more ONs as defined above or any mixtures thereof may be administered in a physiologically acceptable salt solution or buffer, i.e. naked, to a subject, such as a human. The ONs can penetrate the cell through gymnosis.

Alternatively, the one or more ONs as defined above or any mixtures thereof may be administered using a delivery system. In the delivery system, the ONs may be conjugated or formulated or both. Examples of a delivery system may be a pharmaceutical composition comprising the one or more ONs of the invention and optionally one or more of a pharmaceutically acceptable carrier, adjuvant and/or excipient, as is commonly known in the art in this kind of pharmaceutical compositions.

The pH of the pharmaceutical composition is selected so as to be biologically compatible, i.e. a pH between 5 and 8.

The concentration of an ON(s) of the invention in such a delivery system or pharmaceutical composition will depend on e.g. the ON(s), the manner of administrating the ON(s) and the carrier, adjuvant and/or excipient used in the delivery system or pharmaceutical composition. The concentration may be between about 0.1 and 200 mg/ml or between 5 µg/ml and 10 mg/ml.

The delivery system may also comprise carriers, such as nuclear localization signal peptides (NLS), cationic or cell penetrating peptides (CPP). PepFect 14 (PF14) is an example of such a CPP. Other carriers may be uptake enhancers, such as lipophilic compounds that improve cell delivery or pharmacodynamic properties. Excipients may be used to improve solubility, stability and uptake.

The ONs of the present invention may be administered orally, parenteral, buccal, vaginal, rectal, inhalation, insufflation, sublingually, intramuscularly, subcutaneously, topically, intranasally, intraperitoneally, intrathoracically, intravenously, epidurally, intrathecally and intracerebroventricularly.

The optimum dosage and frequency of administration will depend on the particular condition being treated and its severity; the age, sex, size and weight, diet, and general physical condition of the particular patient; other medication the patient may be taking; the route of administration; the formulation; and various other factors known to physicians and others skilled in the art.

The quantity of the one or more ONs to be administered will vary for the patient being treated and will typically vary from about 0.1 up to 1500 mg per dosage per day. For instance, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention.

Experimental Section

In the present invention, Huntington disease (HD) patient cell lines were used as a model to provide evidence for the accuracy and efficiency of the therapeutic method.

Materials and Methods

Oligonucleotides

LNA/DNA ONs were either bought from Eurogentec (Belgium) or synthesized at Nucleic Acid Center, University of Southern Denmark. CAG ONs were designed to target the DNA template strand while CTG ONs (13, 13gap and 19) were designed to target the mRNA and used as controls. CAG ONs were synthesized in different lengths ranging from 10- to 19-mers. The 12-, 13- and 14-mer CAG ONs were synthesized in both phosphodiester (PO) and phosphorothioate (PS) backbone format. The 14-mer CAG PS ON was synthesized in two more versions, one with 2'-O-methyl RNA/LNA, namely: CAG-14PS-OMe. The other version, CAG-14PS-gly had 2'-glycylamino 5-methylcytosine LNA nucleotides substituting the regular cytidines. A number of mismatched and scrambled ONs were used as controls (sequences found in Table 1). An siRNA targeting HTT transcripts in a region outside the CAG repeats, and used previously, was obtained from Sigma. A complete list of the ON sequences can be found in Table 1.

Synthesis of 1R,3R,4R,7S)-1-(4,4'-Dimethoxytrityloxymethyl)-5-[N-(fluoren-9-ylmethoxycarbonyl)glycyl]-7-hydroxy-3-(5-methylcytosine-1-yl)-2-oxa-5-azabicyclo[2.2.1]heptane (2)

Fmoc-glycine (1.51 g, 5.09 mmol) was dissolved in anhydrous tetrahydrofuran (THF) (80 mL). Anhydrous N,N-diisopropylethylamine (DIPEA) (1.8 mL, 10.3 mmol) was added and the mixture was stirred at room temperature (RT) for 15 min. A solution of HATU (1.92 g, 5.05 mmol) in anhydrous dimethylformamide (DMF) (10 mL) was then added and the mixture was stirred at room temperature or between 16 and 25° C. ((RT) for another 15 min.

Finally, a solution of 5'-O-DMT-protected 2'-amino-LNA-5MeC nucleoside 1 (2.96 g, 5.19 mmol); (38) in anhydrous DMF (30 mL) was added and the reaction mixture was stirred at RT for 1 h. The reaction mixture was then diluted with ethyl acetate (EtOAc) (150 mL) and washed successively with saturated aqueous solutions of NaCl (2×100 mL) and NaHCO$_3$ (100 mL). The aqueous phases were back-extracted with EtOAc (200 mL in total), and the combined organic phase was dried over Na$_2$SO$_4$, filtered and evaporated to dryness under reduced pressure. The resulting residue was co-evaporated with toluene (4×15 mL) and then purified by silica gel column chromatography (0-15% MeOH in dichloromethane (DCM), v/v) to afford nucleoside 2 as a rotameric mixture (~0.7:0.3 by $^1$H NMR) as an off-white foam (3.96 g, 90%). R$_f$=0.6 (15% MeOH in DCM, v/v). $^1$H NMR (400 MHz, DMSO-d$_6$) ("0.7H" indicates signal from major rotamer, "0.3H" indicates signal from minor rotamer) δ$_H$ 7.89 (d, J=7.5 Hz, 2H), 7.73 (d, J=7.4 Hz, 2H), 7.60-7.23 (m, 14H, H6), 6.97 (br s, 1H), 6.95-6.89 (m, 4H), 5.97 (d, J=3.7 Hz, 0.7H), 5.91 (d, J=4.1 Hz, 0.3H), 5.39 (s, 0.7H), 5.34 (s, 0.3H), 4.68 (s, 0.3H), 4.41 (s, 0.7H), 4.31-4.14 (m, 4H), 4.12-3.91 (m, 2H), 3.74 (s, 6H), 3.50-3.28 (m, 4H), 1.56 (s), 1.53 (s). $^{13}$C NMR (101 MHz, DMSO-d$_6$) δ$_C$ 168.0, 167.6, 165.4, 158.2, 156.6, 156.5, 154.4, 144.6, 144.5, 143.9, 143.8, 140.7, 136.6, 135.4, 135.3, 135.1, 129.8, 129.7, 128.0, 127.7, 127.6, 127.1, 126.9, 125.3, 120.1, 113.3, 101.0, 100.9, 87.7, 87.1, 87.0, 86.8, 85.8, 85.7, 69.0, 65.7, 62.1, 59.2, 55.1, 55.1, 46.6, 42.5, 13.4, 13.3. HRMS-ESI (m/z): 872.3290 ([M+Na]$^+$, C$_{49}$H$_{47}$N$_5$O$_9$—Na$^+$ calcd 872.3266).

Synthesis of (1R,3R,4R,7S)-1-(4,4'-Dimethoxytrityloxymethyl)-5-[N-(fluoren-9-ylmethoxycarbonyl)glycyl]-7-hydroxy-3-(4-N-benzoyl-5-methylcytosine-1-yl)-2-oxa-5-azabicyclo[2.2.1]heptane (3)

Nucleoside 2 (3.23 g, 3.80 mmol) was dissolved in anhydrous DMF (75 mL). Anhydrous pyridine (1.2 mL, 14.8 mmol) and benzoic anhydride (1.74 g, 7.69 mmol) were added and the reaction mixture was stirred at RT for 42 h. The reaction mixture was then diluted with EtOAc (150 mL) and washed with a saturated aqueous solution of NaCl (4×125 mL). The organic phase was dried over Na$_2$SO$_4$, filtered and evaporated to dryness under reduced pressure. The resulting residue was co-evaporated with toluene (15 mL) and then purified by silica gel column chromatography (0-3% MeOH in DCM, v/v) to afford nucleoside 3 as a rotameric mixture (~0.7:0.3 by $^1$H NMR) as a white foam (2.14 g) containing traces of an unknown impurity (giving a peak at 8.1 ppm in $^1$H NMR spectrum and at 170.1 ppm in $^{13}$C NMR spectrum). R$_f$=0.4 (5% MeOH in DCM, v/v). $^1$H NMR (400 MHz, CDCl$_3$) ("0.7H" indicates signal from major rotamer, "0.3H" indicates signal from minor rotamer) δ$_H$ 12.96 (br s, 1H), 8.29-8.22 (m, 2H, Ar-Bz), 7.79 (s, 0.7H), 7.75 (s, 0.3H), 7.71 (d, J=7.5 Hz, 2H), 7.61-7.20 (m, 18H), 6.84 (dd, J=8.8, 3.4 Hz, 4H), 5.98 (br s, 0.3H), 5.84 (t, J=4.8 Hz, 0.7H), 5.55, 5.54 (2×s, 1H combined), 5.13 (s, 0.3H), 4.74 (s, 0.7H), 4.37 (s, 1H), 4.36-4.05 (m, 5H), 3.784, 3.775 (2×s, 6H combined), 3.64-3.38 (m), 1.82 (s), 1.76 (s). $^{13}$C NMR (101 MHz, CDCl$_3$) δ$_C$ 170.1, 168.7, 168.6, 159.9, 158.86, 158.84, 158.76, 157.1, 156.8; 148.4, 144.6, 144.5, 144.0, 143.9, 143.8, 141.3, 139.6, 136.8, 136.2, 135.5, 135.44, 135.41, 135.3, 133.6, 132.7, 132.6, 130.2, 130.0, 129.7, 129.3, 128.6, 128.3, 128.23, 128.19, 128.0, 127.9, 127.8, 127.2, 125.34, 125.27, 120.0, 113.5, 113.3, 111.8, 89.1, 88.4, 87.5, 87.2, 87.03, 86.95, 70.0, 69.1, 67.5, 63.1, 61.8, 59.1, 55.3, 53.6, 51.6, 47.1, 43.2, 13.9, 13.8. HRMS-ESI (m/z): 976.3494 ([M+Na]$^+$, C$_{56}$H$_{51}$N$_5$O$_{10}$—Na$^+$ calcd 876.3528). This crude product was used without further purification in the next step.

Synthesis of (1R,3R,4R,7S)-7-(2-Cyanoethoxy(diisopropylamino)phosphinoxy)-1-(4,4'-dimethoxytrityloxymethyl)-5-[N-(fluoren-9-ylmethoxycarbonyl)glycyl]-7-hydroxy-3-(4-N-benzoyl-5-methylcytosine-1-yl)-2-oxa-5-azabicyclo[2.2.1]heptane (4)

Nucleoside 3 (2.27 g; material added from several syntheses of 3) and N,N-diisopropylammonium tetrazolide (812 mg, 4.74 mmol) were dissolved in anhydrous DCM (40 mL) at RT under stirring, and 2-cyanoethyl-N,N,N',N'-tetraisopropylphosphane (1.5 mL, 4.72 mmol) was added dropwise. The reaction mixture was stirred at RT for 16 h whereupon EtOH (3 mL) was added and the resulting mixture was stirred for 5 min. The mixture was diluted with DCM (100 mL) and then washed with a saturated aqueous solution of NaHCO$_3$ (2×100 mL). The combined aqueous phase was back-extracted with DCM (3×30 mL). The combined organic phase was dried over Na$_2$SO$_4$, filtered and evaporated to dryness under reduced pressure. The residue was purified by silica gel column chromatography (20-60% EtOAc in petroleum ether, v/v) to afford phosphoramidite 4 as a rotameric mixture of diastereomers obtained as a white foam (2.13 g, 46% from 2). R$_f$=0.6 (5% MeOH in DCM, v/v); $^{31}$P NMR (162 MHz, CDCl$_3$) δ$_P$ 150.3, 149.9, 149.6, 148.5. HRMS-ESI m/z: 1154.4827 ([M+H]$^+$, C$_{65}$H$_{68}$N$_7$O$_{11}$P—H$^+$ calcd 1154.4787).

Cell Culture, Transfections and Gymnosis

Huntington patients' primary fibroblasts GM04281, GM09197 and GM04022 were obtained from the Coriell Cell repositories. GM04281, GM09197 and GM04022 HD fibroblast in this order have numbers of 68/17, 151/21 and 44/12 CAG repeats representing the mutant/wild-type HTT respectively. Fibroblasts were grown in Dulbecco's Modified Eagle Medium (DMEM) with L-glutamine, pyruvate and low glucose (Invitrogen, Sweden), supplemented with 10% fetal bovine serum (FBS) (Invitrogen). Fibroblasts were maintained at 37° C., 5% $CO_2$ in humidified incubators. One day prior to transfection, fibroblasts were seeded at 30,000 cells per well in a 24-well plate or at 160,000 cells per well in a 6-well plate. ONs were formulated either with lipofectamine RNAiMAX™ (RNAiMAX) according to the manufacturer's protocol or with the CPP Pepfect 14 (PF14) in a molar ratio 1:5 (ON: peptide). Formulations were added to the fibroblasts, while still growing in 10% FBS medium, to give a 100 nM final concentration of the ON. Gymnosis was performed by adding the ONs directly to the cells one day after seeding without using transfection reagents. Unless otherwise stated, cells were cultured for four days following transfections, or kept under gymnosis for four days, after which the cells were lysed for RNA or protein assessment.

Fluorescence Microscopy

Cy5 labeled ONs were transfected into GM04281 fibroblasts at 100 nM concentration using RNAiMAX. Before imaging, the medium was aspirated and cells were carefully rinsed using fresh full medium to ensure the removal of any ON or formulation residuals. Live cells were then imaged using a fluorescence microscope (Olympus IX81, Olympus America Inc.) and the signal of the Cy5-labelled ONs was detected.

RNA Isolation and Quantitative Reverse Transcriptase Multiplex PCR (q RT-PCR).

At specific time points, cells were lysed and total RNA isolated using the RNeasy plus kit (QIAGEN, Sweden). RNA was analysed using multiplex q RT-PCR to amplify both HTT and HPRT1 as an endogenous control. This assay was performed using the Quantifast™ Multiplex RT-PCR kit (Qiagen). Sequences of primers and probes for HTT and HPRT (Sigma) were as follows: HTT-fwd: 5'-gactcgaacaagcaagag (SEQ ID NO: 47), HTT-rev: 5'-gcctt-taacaaaaccttaatttc (SEQ ID NO: 48), HPRT-fwd: 5'-gagct-attgtaatgaccagtc (SEQ ID NO: 49), HPRT-rev: 5'-tgac-caaggaaagcaaag (SEQ ID NO: 50), HTT taqman probe: 5'-[JOE]gaagaatcagtccaggagacc[BHQ1] (SEQ ID NO: 51) and HPRT taqman probe: 5'-[6FAM]tgccagtgtcaattatatcttc-cacaa[BHQ1] (SEQ ID NO: 52) where JOE and 6-FAM are two fluorophores having different emission spectra and with Black Hole Quencher (BHQ1) used as quencher. Multiplex q RT-PCR reaction setup was done according to the Quantifast™ kit protocol, where 35 ng of RNA was used for all reactions and the final volume of each reaction was 25 µl. Standard curves were made using known amount of RNA and serially diluted in order to confirm the efficiency of PCR, which was close to 100%. Cycling conditions of PCR were: 20 min 50° C. for reverse transcription, 5 min 95° C. for PCR initial activation step and 45 cycles, each of 2 steps: 15 s, 95° C. denaturation and 30 s, 60° C. for annealing/extension. Quantitative RT-PCR was performed using the StepOnePlus™ Real time PCR system (Applied Biosystems, Sweden) and the data was analysed by the $\Delta\Delta C_t$ method using the StepOne™ software version 2.2.

Western Blotting

Cells in the 6-well plates were lysed using a mixture of RIPA lysis buffer and NuPAGE™ LDS sample buffer (Invitrogen) in a ratio of 3:1 respectively. The plates were kept on ice for 30 min, and then the lysates were transferred to Eppendorf tubes, which were shaken for 30 min at 4° C. to ensure cell lysis. 4 µl of NuPAGE™ sample reducing agent 10× (Invitrogen) were added to 40 µl cell lysate and the mixture was heated to 95° C. for 5 min just before loading on the gel. Proteins were separated on NuPAGE™ 3-8% tri-acetate gels at 70 V for 25 min followed by 125 V for 6 h and the whole electrophoresis procedure was performed on ice at 4° C. The gels were then transferred onto nitrocellulose membranes using the IBlot™ system (Invitrogen) and subsequently the membranes were blocked with Odyssey Blocking Buffer (LI-COR Biosciences GmbH) for 1 h. Membranes were probed using anti-HTT primary antibody (MAB2166, Millipore) and anti-importin 7 antibody, which was used as a housekeeping control, diluted at 1:500 and 1:1000 respectively, over night. Signals were detected after soaking with secondary antibodies, which were goat anti mouse and goat anti rabbit for HTT and importin 7, respectively. For checking the expression of control genes containing CAG repeats, NuPAGE™ Bis-Tris 4-12% gels were used to separate the proteins. After transfer and blocking as before, the membranes were probed with monoclonal Anti-TBP (Tata box binding protein) (Sigma) 1:2000, polyclonal Anti-FOXP2 (Forkhead box protein P2) (Abcam) 1:1000 and polyclonal Anti-ATN1 (atrophoin-1) (Santa Cruz) 1:1000. All western blot signals were scanned using Odyssey Imager from LI-COR Biosciences GmbH.

Thermal UV-Melting Experiments

All Tm experiments were performed using a Varian Cary 300 UV-VIS spectrophotometer. The ON concentrations were 3 µM each in a total volume of 400 µL containing intra-nuclear salt buffer (Tris-acetate 50 mM (pH 7.4), 120 mM KCl, 5 mM NaCl, 0.5 mM Magnesium acetate). The melting profile started at 95° C. and was followed down to 20° C. at 0.2° C./min, and returning to 95° C. at the same rate. Absorbance was recorded at 260 nm and Tm calculated from processed curves using the instrument software algorithms.

Plasmid Cloning and Hybridization Experiments

Plasmid 1735-1 contains a 72 CAG repeat sequence (SEQ ID NO: 54) (216 bp) and was cloned by Mutagenex using standard molecular cloning procedures. The control plasmid contains the same backbone, but lacks the 72 CAG repeat region (SEQ ID NO: 54). ONs and plasmids were hybridized for 72 h at 37° C. in 10 µL using 500 ng of plasmid and 40 pmol of ON in intra-nuclear salt buffer, unless otherwise stated.

Restriction Enzyme Assay of ON Target Binding

Restriction enzymes AvrII (#FD1564) and HindIII (#FD0504) (Thermo Scientific) were incubated with 500 ng plasmid 1735-1 (pre-incubated 24 h with or without 40 pmol CAG-ONs), according to the manufacturer's protocol. The samples were analyzed by PAGE using 20% polyacrylamide gels in TBE (Tris borate EDTA) (Life Technologies). An amount of 200 ng of DNA in DNA Loading Dye buffer (Thermo 6× R0611 diluted to 1× in $ddH_2O$) was loaded into each well. Electrophoresis was performed at 110V for 1.2 h in 1×TBE buffer. The gel was stained using 1×SYBRGold nucleic acid gel stain (Invitrogen #S-11494) for 7 minutes on shaker, visualized using a VersaDoc system (BioRad) and analyzed by the QuantityOne software (BioRad).

Chromatin Immunoprecipitation (ChIP-qPCR)

ChIP-qPCR was performed using the iDEAL ChIP-seq kit for histones (Diagenode, #C01010051) according to the manufacturer's instructions. Briefly, cells were fixed in 1% formaldehyde for 8 minutes and following chromatin extraction aliquots of one million cells were sonicated for 12 cycles of 30s on/off in 1.5 ml Bioruptor Microtubes (Diagenode, #C30010016) 1.5 ml tubes with a bioruptor pico (Diagenode). One million cells were used per immunoprecipitation with 3 µg of antibodies against active histone modifications: histone 3 lysine 4 trimethylation (H3K4me3) (Ab-003-050, Diagenode) and histone 3 lysine 27 acetylation (H3K27ac) (ab4729, Abcam) or 5 µg of RNA Pol II ser2 antibody (ab5095, Abcam). DNA was isolated following reverse cross-linking with QIAquick PCR Purification Kit (QIAGEN). ChIP DNA was diluted for qPCR fifty times.

Briefly 3 µl of diluted ChIP DNA was used per reaction, in triplicate with FastStart Universal SYBR Green Master (Roche). Primers are listed in table 2.

TABLE 2

ChIP-qPCR primers used in the study.

| Primer # | Location | Forward sequence | Sequence No | Reverse sequence | Sequence No |
|---|---|---|---|---|---|
| 1 | HTT TSS | GGTTCTGCTT TTACCTGCGG | SEQ. ID NO: 25 | CTCGGGCCGA CTCGC | SEQ. ID NO: 26 |
| 2 | Exon 1 | GGTCCAAGA TGGACGGC | SEQ. ID NO: 27 | AGCACCGGGG CAATGAAT | SEQ. ID NO: 28 |
| 3 | 5' of CAG repeat | ATTGCCCCG GTGCTGAG | SEQ. ID NO: 29 | GGACTTGAGG GACTCGAAGG | SEQ. ID NO: 30 |
| 4 | Gene body (intron 1) | GCTCCCTCAC TTGGGTCTTC | SEQ. ID NO: 31 | CAAGTTCTCG CCCCAACTCT | SEQ. ID NO: 32 |
| 5 | Gene body (intron 1) | GTCAGGCTT GCCAGAATA CG | SEQ. ID NO: 33 | TGGGGTTCCG CTAGATGTTT | SEQ. ID NO: 34 |
| 6 | Gene body (intron 1) | GAAGACCTT TCTGCTGGGC T | SEQ. ID NO: 35 | TCTCCTTTGT CAAGGCAGCA A | SEQ. ID NO: 36 |
| 7 | Gene body (intron 1) | TTCCTATCTG GTGTTTCCCT GAC | SEQ. ID NO: 37 | TTAACACTCG ATTAACCCTG ACA | SEQ. ID NO: 38 |
| 8 | Gene body (intron 1) | TGAGTAAAG ACCTCAAGC GAGT | SEQ. ID NO: 39 | GAAGATTTTG GACCTGTTCC CCC | SEQ. ID NO: 40 |
| — | Exon 30 | TGGGGACAG TACTTCAAC GC | SEQ. ID NO: 41 | ACCTTGAAAA TGTTTCTTCT GGCA | SEQ. ID NO: 42 |
| — | Exon 67 | TCATCAGCA GGATGGGCA AG | SEQ. ID NO: 43 | AGTCAGCAGC CGGTGATATG | SEQ. ID NO: 44 |

Statistics

Data are expressed as mean±SEM. Statistical analyses were performed using Student's t-test for comparison of means. A probability of less than 0.05 was considered to be statistically significant.

Results

CAG PS ONs can Significantly Down Regulate HTT Gene Expression on Both mRNA and Protein Levels The approach taken was to generate a set of short LNA-DNA mixmers directed against the repeat region in the DNA duplex with the aim of reducing the transcription of the HTT gene. LNA/DNA CAG ONs (12-, 13- and 14-mers) were first designed so that they bind via complementarity to the HTT DNA template strand. Three of the ONs were synthesized with a PO backbone, while the other three were PS ONs. In order to test the efficiency of the ONs, the lipid transfection reagent RNAiMAX was first used as a delivery vehicle to target primary HD patient fibroblasts GM04281. Prominent and reproducible HTT knockdown on both mRNA (FIG. 1a) and protein levels (FIG. 2) could successfully be achieved using the PS ONs. The efficiency of the PS ONs was significantly higher than that obtained by the PO ONs. In order to investigate if the uptake mechanism could be an explanation for such pronounced difference in activity, Cy5-labeled ONs of either PS or PO backbone chemistry were transfected followed by imaging of the live cells by fluorescence microscopy 4 days after transfection. The PS ONs showed distinct nuclear localization, while the POs were mainly seen in the cytoplasm (FIG. 1b). When HTT protein levels were monitored 7 days after a single-dose transfection, the same knockdown efficiency of the PS ONs could still be observed (FIGS. 2c and 2d). Control ONs (mismatched ON1 and mismatched ON2) did not cause any reduction in HTT mRNA (FIG. 1a) or HTT protein levels (FIG. 2).

Effect of the ON Length on the HTT Knockdown Efficiency and Allele Selectivity

Figure 3:
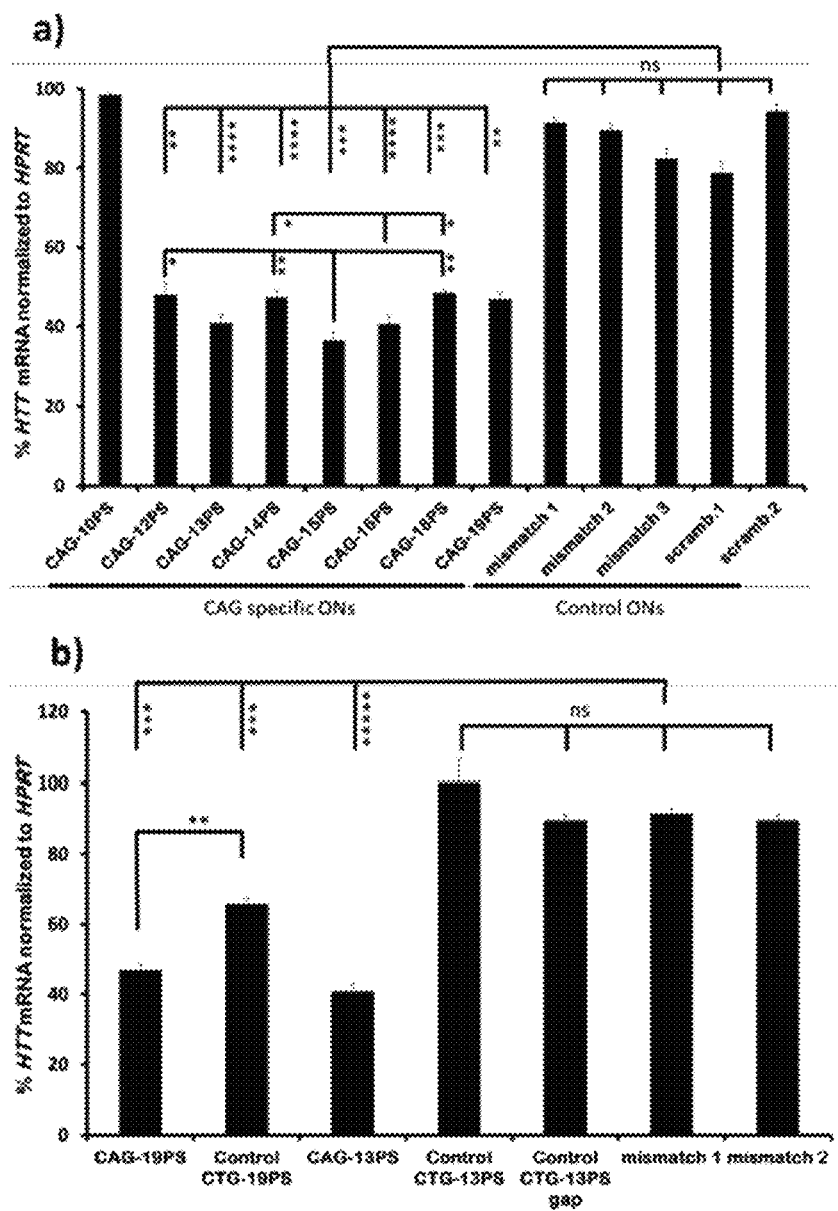
FIG. 3. (a) Effect of the ON length on the HTT mRNA knockdown efficiency. LNA/DNA CAG 10- to 19-mer PS ONs were transfected at 100 nM concentration into GM04281 human HD fibroblasts using RNAiMAX. Four days post treatments, cells were lysed and RNA was isolated and analysed by q RT-PCR using primers and probes for HTT and for HPRT as a housekeeping reference gene. HTT mRNA levels after treatment with CAG-12, -13, -14, -15, -16, 18- and -19 were all significantly reduced as compared to CAG-10PS and to all the mismatched and scrambled controls (significance levels between each ON and the scrambled ON1 are shown in the figure). CAG-15PS differed significantly as compared to CAG-12PS, CAG-14PS and CAG-18PS. CAG-16 PS differed also significantly as compared to CAG-14PS and CAG-18PS. No other significant differences were found between the ONs from 12 to 19-mer in HTT mRNA knockdown levels. (b) CAG ONs down regulate HTT mRNA more potently as compared to control CTG ONs. 13- and 19-mer ONs of either CAG or CTG sequence were transfected into HD fibroblasts GM04281 for 4 days and the remaining HTT mRNA levels were assessed using q RT-PCR. A significant difference was found between the remaining HTT mRNA levels after CAG-19PS versus control CTG-19PS treatment ($p<0.01$) and they were both significantly different from the control ON (mismatched 1) ($p<0.001$ and $p<0.001$). CAG-13PS effect was significantly different from mismatched 1 ON ($p<0.00001$). CTG-13PS and CTG-13PS control ONs did not show any significant difference compared to the control mismatched ONs used in the study.
Figure 4:
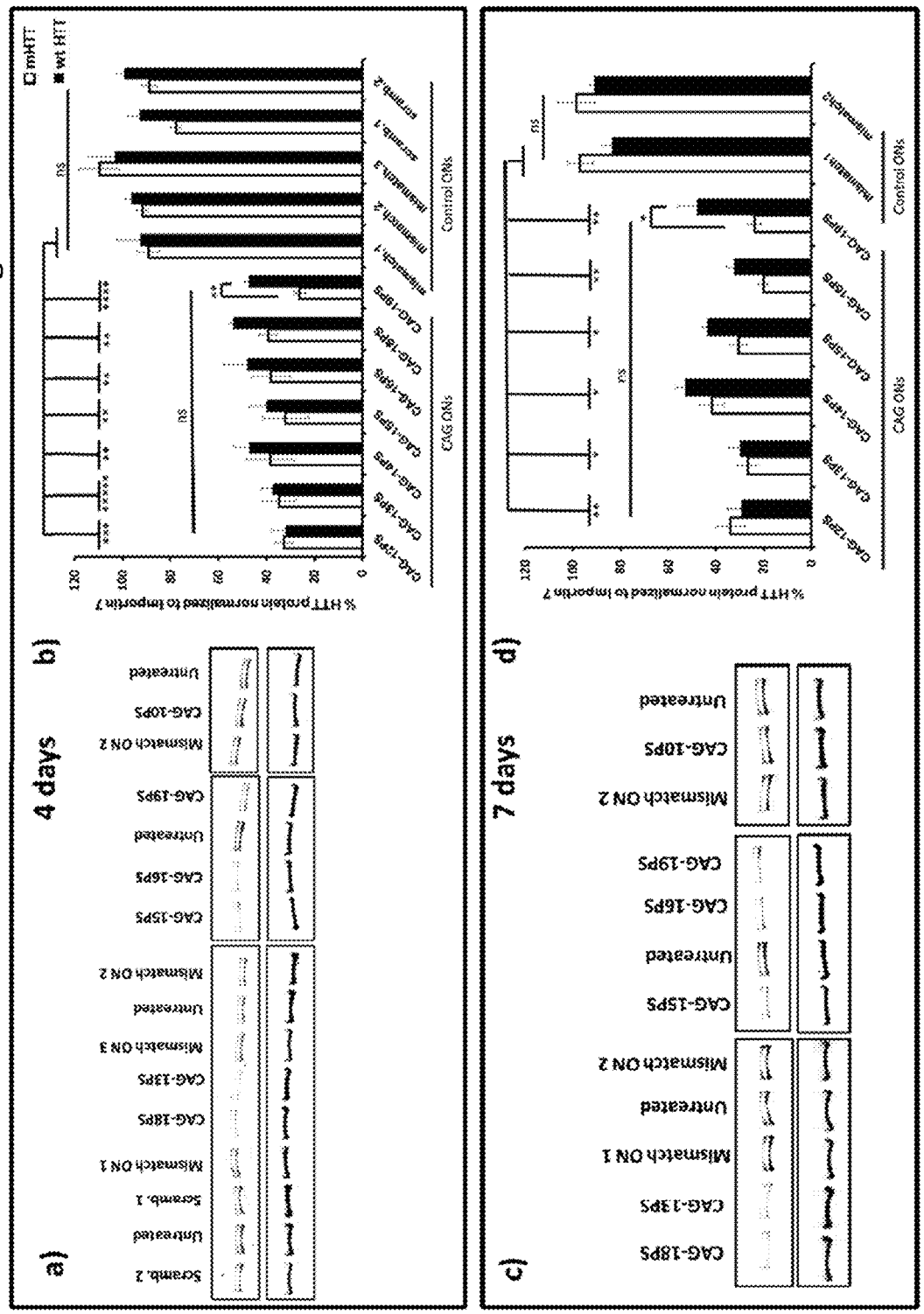
FIG. 4. Effect of the ON length on the HTT protein knockdown efficiency and allele selectivity. LNA/DNA CAG 10- to 19-mer PS ONs were transfected at 100 nM concentration into GM04281 human HD fibroblasts using RNAiMAX. Four or seven days post treatments, cells were lysed and western blots were performed to detect the HTT protein with its two isomers: muHTT and wtHTT. Importin 7 was used as a housekeeping control. (a) Shows a representative western blot gel for the 4 days-time point, while (c) shows a representative gel for 7 days. Results from three replicate experiments were quantified and plotted in (b) and (d) for the 4 and 7 days data respectively. Total HTT protein levels remained after treatments with ONs (from 12 to 19-mers) were significantly different from all control ONs tested in the study. Significance levels between each CAG ON and the control ON (mismatched 1) are shown in the figure (b) and (d). No significant difference was found between the control ONs used in the study. A significant difference was found between the remaining muHTT and wtHTT protein levels 4 and 7 days after treatment with CAG-19PS (p<0.01 and p<0.05 respectively).

It was tested how changing of the CAG PS ON length would affect HTT down regulation. Shortening the ON into a 10-mer completely abolished the effect, while ONs of 15-, 16-, 18- and 19-mer length significantly reduced HTT mRNA to levels, similar to the previously evaluated 12-, 13- and 14-mers (FIG. 3a). The percentage of remaining HTT mRNA ranged from 35-50%. Reduced HTT protein levels were observed 4 days after transfecting HD patient fibroblasts with the CAG PS ONs (FIGS. 4a and 4b). The reduction in HTT protein levels was significant compared to all the control ONs tested in the same experiments. A dose response curve was made to one of the ONs (CAG-16PS) both on mRNA and protein levels. Moreover, the knockdown effect of protein levels lasted for 7 days after single-dose transfections (FIGS. 4c and 4d). There was no significant difference between the effects on the muHTT versus wtHTT protein levels using the shorter ONs. However, the longest ON used in the study (CAG-19PS) showed significantly higher reduction of the muHTT protein as compared to the wtHTT after both 4 and 7 days (FIGS. 4b and 4d). To further investigate whether the effect starts at earlier time points and if it lasts for longer ones, a kinetics study was conducted and showed that the down regulation of HTT started 1 day post transfection (although effect was significantly different from that got 4 days after). Efficiency of the ONs was even still detected up to 10 days, which was the last time point tested in the study. Then selected CAG ONs were also tested in 2 other HD fibroblasts cell lines: one with a higher repeat number (GM09197) and the other with lower number (GM04022). Interestingly, the selected CAG ONs showed efficiency in both cell lines similar to that obtained in the GM04281.

CAG ONs do not Affect the Expression of other CAG Repeat Containing Genes

Other housekeeping genes also contain tracts of CAG repeats. In order to evaluate the potential for off-target effects of the studied CAG ONs, the expression levels of control genes was checked after treating the GM04281 HD fibroblasts. Western blot analysis showed no effect for CAG ONs compared to scrambled ONs on the expression levels of TBP, which contains CAG repeat tracts of up to 19 repeats in the coding region, FOXP2, containing a mixed stretch of 40 CAG and CAA repeats in the 5'-UTR, or on levels of ATN1 holding 15 CAG repeats (SEQ ID NO: 55).

CAG ONs more Potently Down Regulate HTT mRNA as Compared to CTG ONs

Figure 5:
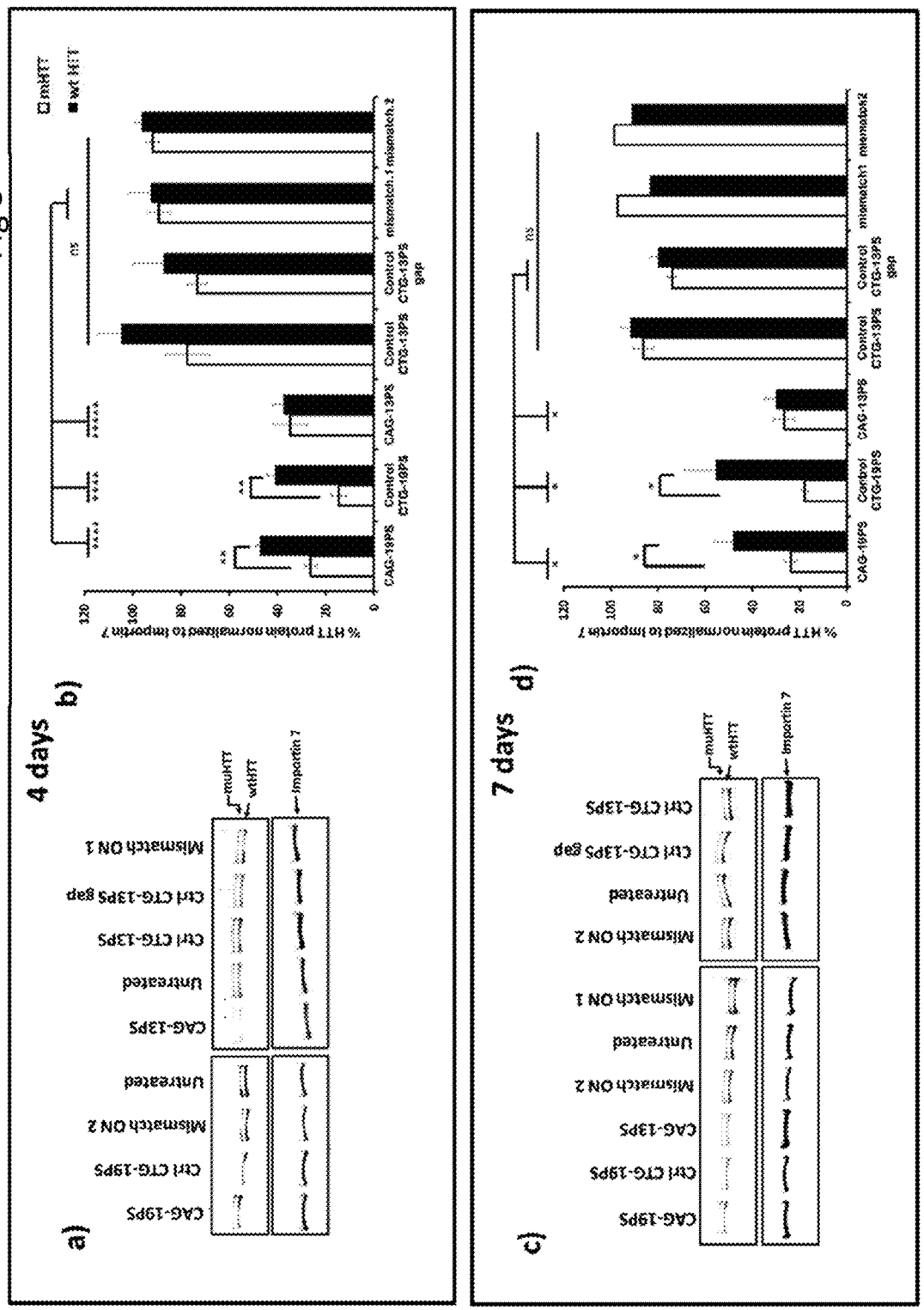
FIG. 5. CAG ONs versus control CTG ONs in HTT protein down regulation efficiency. 13- and 19-mer ONs of either CAG or CTG sequence were transfected into HD fibroblasts GM04281 for 4 days or 7 days followed by cell lysis and western blots. (a) and (c) show representative western blot gels for the 4 and 7 days data respectively. Quantification of western blot gels is shown in (b) for the 4 days and (d) for the 7 days results. Significant difference was found between the remaining muHTT and wtHTT protein levels 4 and 7 days after treatment with CAG-19PS (p<0.01 and p<0.05) and with control CTG-19PS (p<0.01 and p<0.05). No other significant difference was found between muHTT and wtHTT after treatment with any other ON. Total HTT protein was significantly reduced after treatment with CAG-19PS, control CTG-19PS and CAG-13PS as compared to the mismatched controls (significance levels between each ON and mismatched 1 are shown in the figures (b) and (d). Control CTG-13PS and 13PSgap were not significant compared to the mismatched control ONs.

Knocking down HTT mRNA by a single-stranded ON can be achieved using either an ON that binds to mRNA and induces RNase H degradation or an ON that binds to DNA and blocks its transcription. To exclude that the HTT mRNA down regulation effect obtained here could be due to mRNA binding, the CAG ONs were compared side by side to ONs complementary to the HTT mRNA i.e. CTG ONs. Two 13-mer LNA/DNA CTG control ONs: CTG-13PS and CTG-13PS gap (Table 1), which differ in the distribution of LNA and DNA base composition, were designed and tested in GM04281 HD fibroblasts. None of the control CTG ONs caused any reduction of the HTT mRNA as compared to the CAG-13PS, which significantly did (FIG. 4a). A 19-mer LNA/DNA CTG ON (control CTG-19PS) resulted in some reduction in HTT mRNA (35%), as was previously reported, and further discussed below. Thus, the remaining HTT mRNA level after transfection of control CTG-19PS (65%) was significantly higher than that obtained after transfection of CAG-19PS (43%) (FIG. 3b). As expected, transfection with the control CTG-19PS ON caused a marked reduction in Huntingtin protein with a significantly enhanced effect on the mutated protein after both 4 and 7 days (FIG. 5). This observation indicates that the CAG ONs, which down regulate HTT on the mRNA level, are working via a mechanism that does not involve binding to mRNA, but is instead compatible with an effect caused by binding to the HTT gene.

UV Melting Measurements

Figure 6:
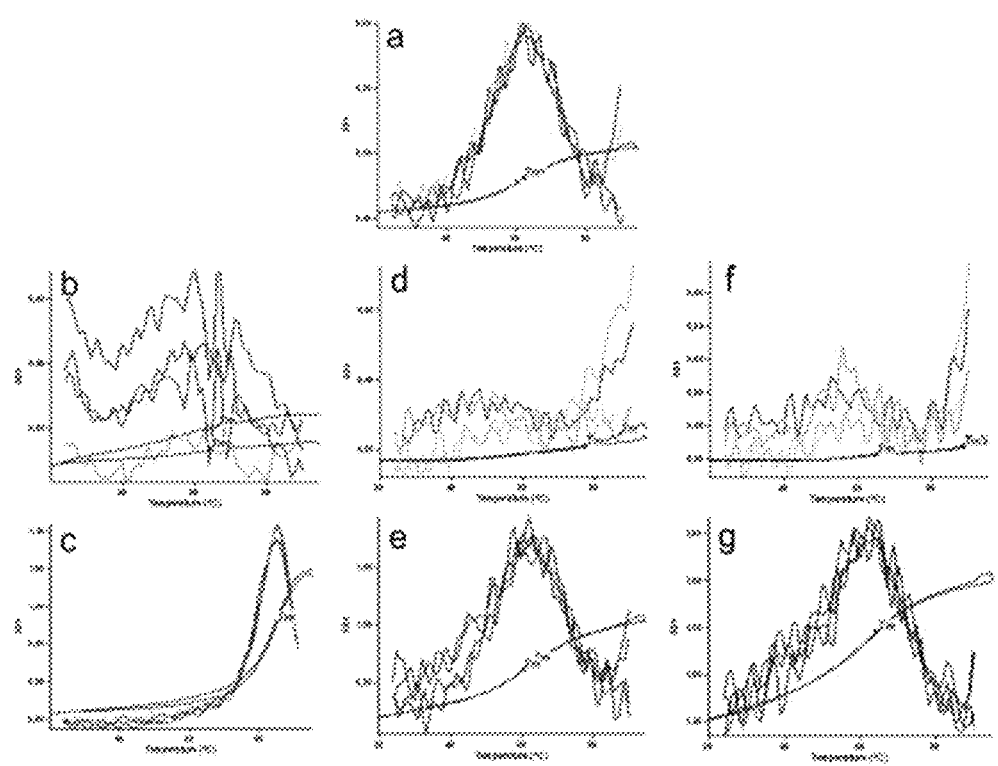
FIG. 6. UV melting profiles of CAG, CTG and target RNA ONs. All graphs show the Tm curves (marked 'Tm' in the figure) together with the second derivative in the background. (a) target RNA alone, (b) CTG13 alone, (c) RNA+CTG13, (d) CAG13 alone, (e) RNA+CAG13, (f) CAG19 alone and (g) RNA+CAG19. Only CTG13 is capable of binding the target RNA and shift the Tm above the baseline of the RNA ON alone.

To further confirm that the CAG ONs do not bind to the RNA sense sequence, Tm was measured for the combination of CAG-13PS and RNA (19-mer CAG ON) and compared to that of control CTG-13PS and RNA. The RNA used as target was a 19-mer CAG ON and the analysis showed no evidence of any interaction between the CAG-13PS and the RNA, since there was no shift in the Tm curve (FIG. 6e). On the other hand, control CTG-13PS combined with the RNA target sequence markedly shifted Tm>20° C. indicating binding and interaction on the RNA level (FIG. 6c). In addition, the CAG-19 ON together with the RNA showed no binding either (FIG. 6g). Due to the large shift in Tm (>95° C.) that the control CTG-19 ON together with the RNA would generate, this combination was never tested. Only the target 19-mer CAG RNA ON alone (FIG. 6a) gave a Tm around 62° C., indicating self-interactions not present in the CAG-13, CAG-19 or control CTG-13 ONs.

CAG ONs can Bind to and Invade dsDNA as Evidenced in a Restriction Enzyme Assay

Figure 7:
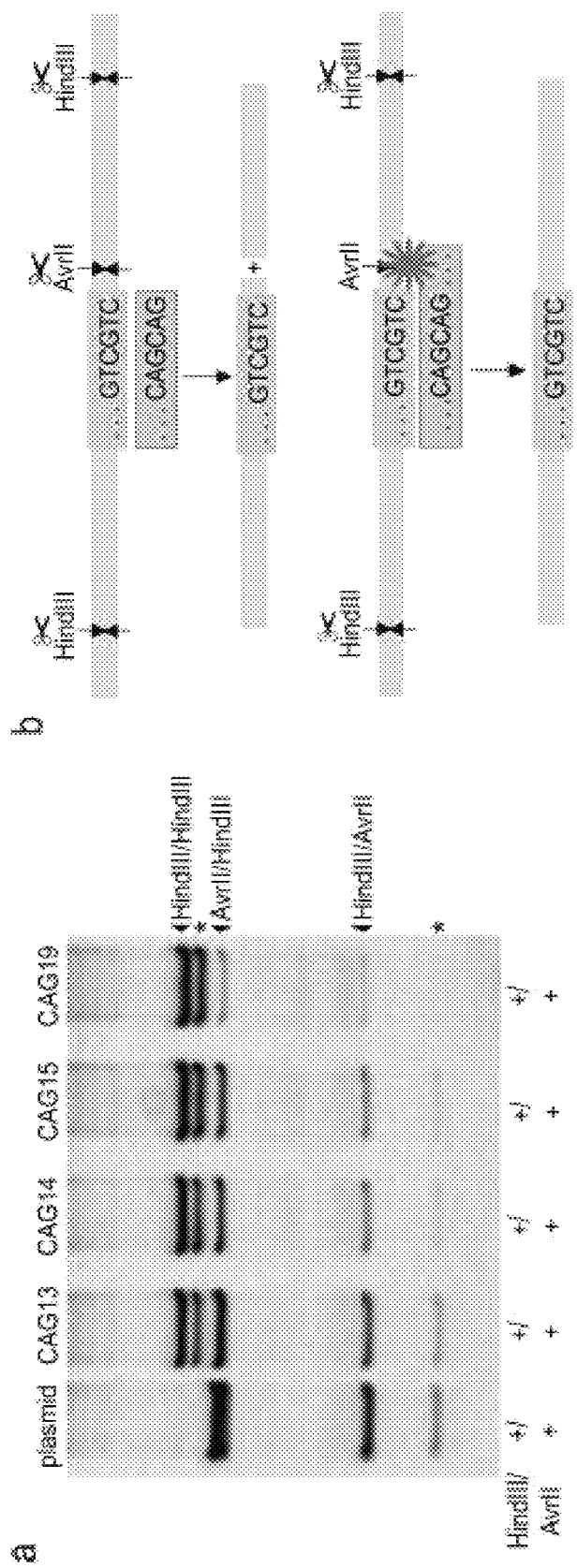
FIG. 7. Binding of CAG ONs to target plasmid DNA visualized by restriction digestion and PAGE. (a): shows the gel lanes with control and ON-hybridized plasmids digested with HindIII and AvrII, as indicated. * Denotes bands believed to originate from a subclone containing a truncated repeat region. (b): schematically illustrates the mechanism by which the ONs hinder the cleavage by AvrII. Upper panel shows the cleavage pattern when no part of the binding ON is interfering with AvrII cleavage. Lower panel shows that longer ON binding randomly increases the probability of steric blocking of the Avr-site.

To further investigate the proposed dsDNA strand-invasion mechanism, it was tested if the CAG ONs could bind to and invade supercoiled dsDNA. To study this, restriction enzymes cleaving near the ON binding sites were used. The change in cleavage pattern resulting from ON steric blocking of enzyme activity has previously been described in a triple-helix context. Plasmid 1735-1, which contains a repeat region consisting of 72 CAG triplets (SEQ ID NO: 54), was hybridized to CAG ONs (13-, 14-, 15- or 19-mers) for 72 h at 37° C. This plasmid contains restriction enzyme sites for AvrII and HindIII, which were used in combination to linearize the plasmid prior to gel electrophoresis (FIG. 7). HindIII cleaves the plasmid at two sites, one located 40 bp upstream of the CAG repeat region and the other 742 bp 3' of this region. AvrII cuts at a site located only a single bp after the CAG repeat region. Together they are expected to generate two fragments; however, as seen in (FIG. 7b), the cleavage by AvrII is hindered by the presence of a CAG ON. Moreover, the longer CAG ON used, the less effective was AvrII digestion, as indicated by the weaker band generated with AvrII and the appearance of the band corresponding to HindIII cleavage only (FIG. 7). The favoured interpretation is that this is seen because a long CAG ON would have a greater probability to interfere with AvrII cleavage due to steric hindrance. The weaker bands seen in the gel (marked by a '*'), which also follow this pattern, likely originate from a different plasmid sub-clone, which exists as a small fraction lacking a part of the 72 CAG region (SEQ ID NO: 54) due to replication errors during plasmid preparation (FIG. 7a).

Figure 8:
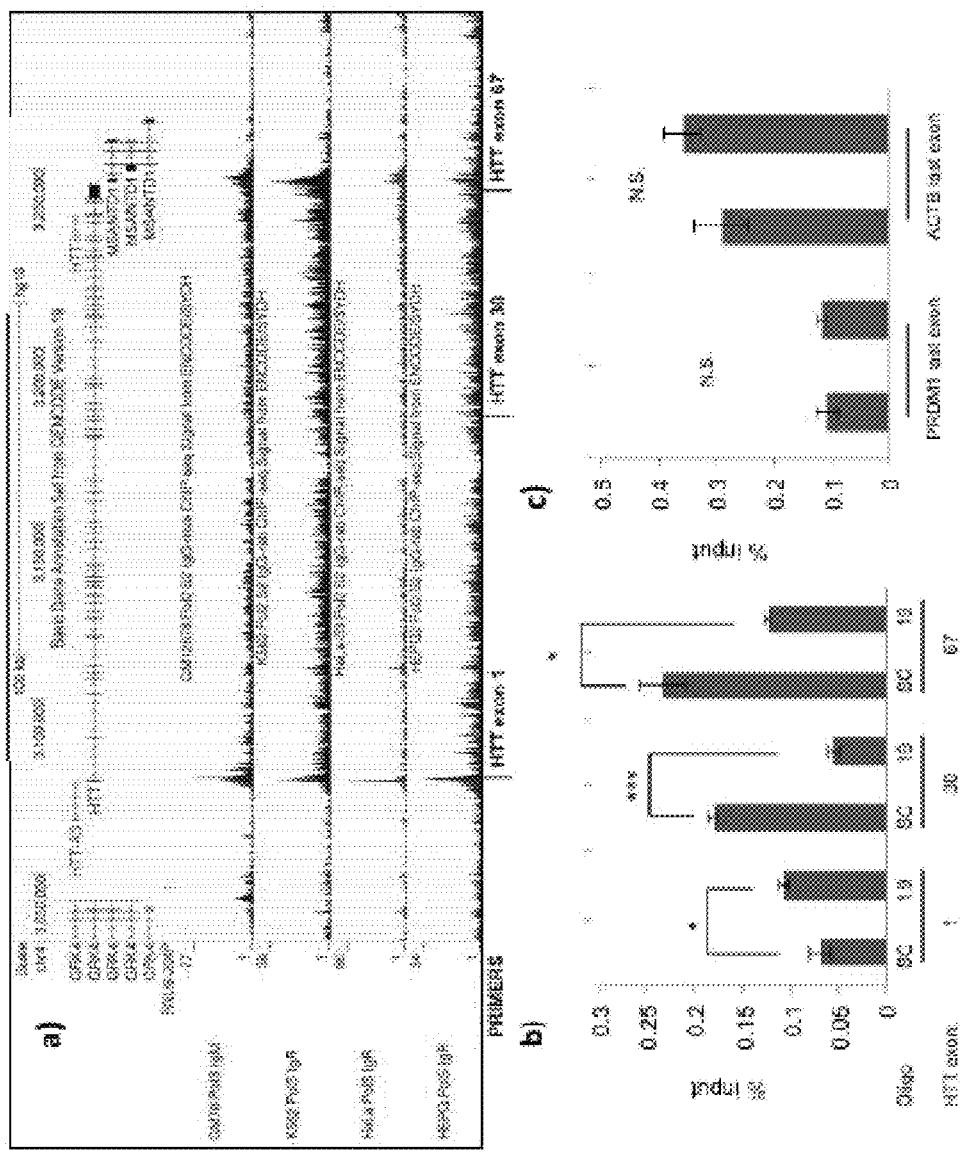
FIG. 8. Serine 2 phosphorylated RNA Pol II occupancy across the HTT gene is reduced upon transfection with HTT targeting oligos. (A) UCSC genome browser image demonstrating RNA Pol II ser2 occupancy across the HTT gene. Primer positions at exon 1 upstream of the CAG repeat and at exons 30 and the last exon, 67, are indicated. (B) RNA pol II occupancy is significantly increase at exon 1 of the HTT gene immediately upstream of the CAG repeat (*p<0.05) and reduced at the 3' exons 30 and 67 (*p<0.05, ***p>0.001). (C) No difference is observed at control loci in the last exons of the PRDM1 or ACTB genes.

CAG ONs Significantly Reduce Serine 2 Phosphorylated RNA Pol II Occupancy Across the HTT Gene To examine if the reduction in HTT gene expression was associated with epigenetic inactivation of the HTT promoter or reduced promoter activity ChIP-qPCR was performed for active histone marks histone 3 H3K4me3 and H3K27ac, which are associated with the transcription start site (TSS) of actively transcribed genes. Primers were designed across the HTT gene 5' region using ChIP-seq data from the ENCODE project to map to locations associated with active histone modifications across the HTT gene in normal conditions. No significant loss of either H3K4me3 or H3K27ac was observed suggesting the HTT targeting CAG ONs function independently of promoter activation and silencing. However, a trend towards increased histone acetylation (p=0.67, t-test) was still observed at the region immediately upstream of the CAG repeat sequence in cells transfected with the HTT targeting oligonucleotide. It was hypothesized this may be linked to slower transcriptional elongation rate at this region of the HTT gene leading to slight hyper-acetylation of chromatin upstream of the CAG repeat region. Given that the HTT targeting ON binds to the HTT gene in the first exon downstream of the TSS and Pol II initiation site it was hypothesized that the targeting ON (CAG-19PS) may influence Pol II elongation in transfected cells which can be examined through measuring serine 2 phosphorylated RNA Pol II occupancy. Serine 2 phosphorylation of RNA Pol II occurs during productive elongation of Pol II following initiation and Pol II ser2 occupancy in the 3' exons of genes is correlated to gene expression and elongation rates. PCR primer positions relative to RNA Pol II ser2 occupancy across the HTT gene in human cell lines is shown in FIG. 8a. Interestingly, CAG-19PS did indeed reduce the 3' occupancy of Pol II ser2 in the HTT gene showing a slight increase of Pol II at the 1st exon upstream of the CAG repeat region (FIG. 8b). It was observed that Pol II ser2 occupancy was higher upstream of the CAG repeat region but significantly reduced in the middle and 3' end of the gene at exons 30 and 67 respectively. This provided conclusive proof that the mechanism of HTT mRNA reduction is mediated through a direct effect on transcription at the level of RNA Pol II elongation suggesting binding of the ON in living cells poses a barrier to HTT gene transcription. No differences were observed at control loci in the last exons of the PRDM1 or ACTB genes (FIG. 8c).

CAG ONs can be Delivered to Patient Fibroblasts by Peptide and Gymnotic Delivery PF14, a recently developed cell-penetrating peptide (CPP) (41), was tested as a delivery vehicle for the LNA/DNA CAG ONs. ON/PF14 formulations at molar ratio 1:5 resulted in similar activity as that obtained by RNAiMAX formulations with CAG-13PS to 19PS (FIG. 9a). PF14/CAG-12PS formulation was less efficient than that with RNAiMAX. Of great interest for CNS delivery is the ability of the ONs to enter the cells without any delivery agent, a phenomenon sometimes referred to as "gymnosis". ONs were added to the HD patient fibroblasts at a concentration of 1 μM without using transfection reagents. Similar and significant levels of HTT mRNA knockdown was achieved with CAG-PS 13-, 14-, 15-, 16-, 18- and 19-mers when compared to control ONs while the 12-mer was less efficient (FIG. 9a). Interestingly, the control CTG-19PS HTT mRNA blocking effect could not be detected using PF14 or gymnotic delivery (FIG. 9a), whereas similar to the data presented in FIG. 3b, RNAiMAX induced a reduction. An siRNA designed against HTT mRNA was used as a positive control for the down regulation. The siRNA was highly efficient only after transfection reagent-aided delivery, but not with gymnosis. CAG-PS ONs (13- and 14-mers) showed markedly and significantly higher efficiency compared to PO ONs when formulated with PF14, similar to what was seen with RNAiMAX formulations (FIG. 9b). Gymnosis of CAG-ONs with PO chemistry unexpectedly caused death of the fibroblasts grown for 7 days following the addition of the ONs. In contrast, the PS ONs were biocompatible, with fibroblasts showing no signs of toxicity by visual inspection (data not shown).

Effect of ON Chemical Modifications on Efficiency

Finally, it was assessed how other types of chemical modification of the ONs could affect the silencing efficiency. CAG-14PS-OMe is a 14-mer CAG ON, with all DNA bases exchanged for 2'-O-methyl RNA bases (Table 1). CAG-14PS-gly is another 14-mer CAG in which four LNA cytosine nucleotides were exchanged by 2'-glycylamino 5-methylcytosine LNA nucleotides (Table 1). Using RNAiMAX, parent CAG-14PS showed significantly better down regulation efficiency than the two ONs with the modifications. However, gymnotic delivery of the three ONs at 1 μM gave the same activity (FIG. 10a). A dose-response curve for gymnosis of the three ONs was generated, which revealed that a 50% knocking down of HTT mRNA can be achieved after gymnosis at 0.5 μM of the parent 14-mer, while the two modified 14-mers need to be present at almost double this concentration in order to give a 50% reduction (FIG. 9b). There were slight differences (not significant) in the dose-response curves, demonstrating that adding these modifications (in terms of type and number of modified bases) could not significantly improve the down regulation efficiency of the CAG ON.

Method for the Diagnosis of Huntington's Disease by Determining the CAG Repeat Length and Sequence Composition Using ON Probes and Sequencing or PCR Amplification The ONs can bind and disrupt non-B-DNA structures associated with the CAG/CTG repeat stretch in the HTT gene. Any one or more of the ONs as defined above can thus be used in a method for the diagnosis of Huntington's disease to facilitate read-through with the aim of determining sequence and length of the affected gene. For this, a method comprising or consisting of the following steps can be used:

1) isolating genomic DNA from a biological sample, optionally cleaving the isolated DNA using for example DNA restriction enzymes, CRISPR-Cas9 based DNA cleavage or by fragmentation using ultra sonication, 2) adding one or more of the ONs as defined above, and 3) determining length and sequence and/or number of CAG/CTG repeats in the HTT gene.

In addition to HTT and diagnosis of Huntington's disease, the method may also be used more generally to determine the sequence and length of any CAG/CTG repeat sequence containing the hairpin, and/or cruciform, non-B-DNA structures since the method to achieve this would be identical.

The biological sample from step 1, typically contains genomic DNA derived from cells and is derived from either blood, cerebrospinal fluid or from a tissue. The method described here can also be used for research purposes, in which case the sample can also come from cell culture or be of bacterial or fungal origin containing the CAG/CTG repeat sequence. The isolation of genomic DNA may be done using any known technique for doing so. Many commercial kits exist that can be used depending on the sample used, and would be known to a person skilled in the art. Likewise, RNA and proteins are typically removed by RNase and other enzyme treatment using methods known to persons skilled in the art. The cleavage of DNA from step 1 can optionally be done using one or more DNA restriction enzymes or sequence-directed cleavage (e.g. CRISPR-Cas9 technology) to improve sample preparation and enrichment before analysis. Alternatively, fragmentation can be achieved by ultra-sonication, both according to protocols known to persons skilled in the art. In PCR and sequencing analysis, this step may help dissolve dissociation of DNA structures, but is considered optional since it is not a requirement for successful analysis. Following step 1, one or more of the ONs as defined above are added in step 2. For example, an ON containing LNA substitutions and the sequence $(CAG)_n$ or $(CTG)_n$, which will invade, hybridize to and thus disrupt the secondary structures in the DNA target sequence in the HTT gene. The binding will not interfere with the analysis method described here, rather, it will facilitate analysis, since ON binding will disrupt the secondary structures that otherwise would reduce analysis efficacy. These secondary structures of DNA are in fact known to cause problems in PCR and sequencing approaches currently used for determining CAG/CTG repeat target length and sequence. Thus, the abolishment of these structures can greatly improve analysis success and accuracy after binding of the ONs described in the document.

Step 3 uses a standard analysis method for determining the length, sequence and number of CAG/CTG repeats in the sample, such as standard PCR or DNA sequencing methods known to a person skilled in the art. The exact sequence and CAG/CTG repeat length in the sample is then compared to the CAG/CTG repeats seen in healthy individuals to determine if the person is diagnosed with HD or is at risk of developing Huntington's disease, or could be associated with other genetic markers that could affect the disease phenotype.

If PCR is used, this typically involves primers complementary to the genomic region of exon 1 in the HTT gene, flanking the repeat region to 3' and 5'. These primers are typically 10-50 nucleotides long. The PCR reaction normally starts with a DNA denaturation step for 1-20 min. Prior to this, a thermal enzyme activation step may be performed if the specific PCR kit used requires this. Following this, an annealing step is utilized when primers bind to the template allowing the polymerase to start polymerization. The last step in PCR is the extension phase where the polymerase is copying the template by complementary adding dNTPs 5' to 3' reading the template 3' to 5'. These steps are then repeated in 20-40 cycles. After PCR, the products are analysed using gel electrophoresis in which also a DNA ladder is analysed to determine the correct length of the amplicons.

If sequencing is used, typically the following steps are involved. Step one is denaturation of the template DNA, double stranded DNA becomes single stranded. Step two is annealing of one primer complementary to a region flanking the CAG/CTG repeats in exon 1 of the HTT gene. In contrast to PCR, only one primer is added so only one strand is copied. Step three is the extension phase, in which dNTPs or ddNTPs are added 5' to 3' reading the template 3' to 5' adding nucleotides complementary to the template. When a ddNTP is incorporated, the reaction stops due to the lack of an OH group at the 3' position. After sequencing, the samples can be analysed using gel electrophoresis as with PCR above. Alternatively, the samples may also be analysed in an automated sequencer where fluorescently labelled nucleotides are used to determine the sequence. Each nucleotide has its own colour, allowing for a spectrophotometer to determine the exact sequence as the labelled fragments passes through a gel. Alternative sequencing platforms may also be used such as Nanopore or PacBio sequencing technologies and other method where amplification is not needed.

SEQUENCE LISTING

```
<160> NUMBER OF SEQ ID NOS: 55

<210> SEQ ID NO 1
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(30)
<223> OTHER INFORMATION: CAG are repeated n times, n is typically about
      3-30. The number of repeats, n, need not to be an integer, and a
      sequence where the majority of the repeats are CAG, and where
      the first complete repeat is optionally preceded by a G or an
<220> FEATURE:
<221> NAME/KEY: misc_feature
<222> LOCATION: (1)..(30)
<223> OTHER INFORMATION: continued from above; AG, and/or where the last
      repeat is optionally followed by a C or a CA

<400> SEQUENCE: 1
cagcagcagc agcagcagca gcagcagcag cagcagcagc agcagcagca gcagcagcag      60
cagcagcagc agcagcagca gcagcagcag                                      90

<210> SEQ ID NO 2
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: oligonucleotide, any nucleotide may be replaced
      with 2'-O-methyl nucleotide
<220> FEATURE:
<221> NAME/KEY: misc_feature
<222> LOCATION: (1)..(30)
<223> OTHER INFORMATION: CAG are repeated n times, n is typically about
      3-30. The number of repeats, n, need not to be an integer, and a
      sequence where the majority of the repeats are CAG, and where
      the first complete repeat is optionally preceded by a G or an
```

```
<220> FEATURE:
<221> NAME/KEY: misc_feature
<222> LOCATION: (1)..(30)
<223> OTHER INFORMATION: continued from above; AG, and/or where the last
      repeat is optionally followed by a C or a CA

<400> SEQUENCE: 2
cagcagcagc agcagcagca gcagcagcag cagcagcagc agcagcagca gcagcagcag      60
cagcagcagc agcagcagca gcagcagcag                                      90

<210> SEQ ID NO 3
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: oligonucleotide, any nucleotide may be replaced
      with 5-propargylamino nucleotide
<220> FEATURE:
<221> NAME/KEY: misc_feature
<222> LOCATION: (1)..(30)
<223> OTHER INFORMATION: CAG are repeated n times, n is typically about
      3-30. The number of repeats, n, need not to be an integer, and a
      sequence where the majority of the repeats are CAG, and where
      the first complete repeat is optionally preceded by a G or an
<220> FEATURE:
<221> NAME/KEY: misc_feature
<222> LOCATION: (1)..(30)
<223> OTHER INFORMATION: continued from above; AG, and/or where the last
      repeat is optionally followed by a C or a CA

<400> SEQUENCE: 3
cagcagcagc agcagcagca gcagcagcag cagcagcagc agcagcagca gcagcagcag      60
cagcagcagc agcagcagca gcagcagcag                                      90

<210> SEQ ID NO 4
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: oligonucleotide, any nucleotide may be replaced
      with 2'-aminoglycyl nucleotide
<220> FEATURE:
<221> NAME/KEY: misc_feature
<222> LOCATION: (1)..(30)
<223> OTHER INFORMATION: CAG are repeated n times, n is typically about
      3-30. The number of repeats, n, need not to be an integer, and a
      sequence where the majority of the repeats are CAG, and where
      the first complete repeat is optionally preceded by a G or an
<220> FEATURE:
<221> NAME/KEY: misc_feature
<222> LOCATION: (1)..(30)
<223> OTHER INFORMATION: continued from above; AG, and/or where the last
      repeat is optionally followed by a C or a CA

<400> SEQUENCE: 4
cagcagcagc agcagcagca gcagcagcag cagcagcagc agcagcagca gcagcagcag      60
cagcagcagc agcagcagca gcagcagcag                                      90

<210> SEQ ID NO 5
<211> LENGTH: 90
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: oligonucleotide, any nucleotide may be replaced
      with piperazino-modified 2'-aminonucleotides
<220> FEATURE:
<221> NAME/KEY: misc_feature
<222> LOCATION: (1)..(30)
<223> OTHER INFORMATION: CAG are repeated n times, n is typically about
      3-30. The number of repeats, n, need not to be an integer, and a
      sequence where the majority of the repeats are CAG, and where
      the first complete repeat is optionally preceded by a G or an
<220> FEATURE:
<221> NAME/KEY: misc_feature
<222> LOCATION: (1)..(30)
<223> OTHER INFORMATION: continued from above; AG, and/or where the last
      repeat is optionally followed by a C or a CA

<400> SEQUENCE: 5
cagcagcagc agcagcagca gcagcagcag cagcagcagc agcagcagca gcagcagcag      60
cagcagcagc agcagcagca gcagcagcag                                      90

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cagcagcagc                                                             10

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cagcagcagc ag                                                          12

<210> SEQ ID NO 8
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cagcagcagc agc                                                         13

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cagcagcagc agca                                                        14

<210> SEQ ID NO 10
<211> LENGTH: 14
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: oligonucleotide, nucleotide may be replaced
      with 2'-O-methyl nucleotide

<400> SEQUENCE: 10
cagcagcagc agca                                                         14

<210> SEQ ID NO 11
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 2'-glycylamino 5-methylcytosine
<220> FEATURE:
<221> NAME/KEY: modified_base
<222> LOCATION: (7)..(7)
<223> OTHER INFORMATION: 2'-glycylamino 5-methylcytosine
<220> FEATURE:
<221> NAME/KEY: modified_base
<222> LOCATION: (10)..(10)
<223> OTHER INFORMATION: 2'-glycylamino 5-methylcytosine
<220> FEATURE:
<221> NAME/KEY: modified_base
<222> LOCATION: (13)..(13)
<223> OTHER INFORMATION: 2'-glycylamino 5-methylcytosine

<400> SEQUENCE: 11
cagcagcagc agca                                                         14

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cagcagcagc agcag                                                        15

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cagcagcagc agcagc                                                       16

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cagcagcagc agcagcag                                                     18
```

```
<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cagcagcagc agcagcagc                                                19

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gacgacgacg acgacga                                                  17

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gacgacgacg acgacga                                                  17

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aagaagaaga ag                                                       12

<210> SEQ ID NO 19
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aagaagaaga agaa                                                     14

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
caacagcagc aacagcaa                                                 18
```

<210> SEQ ID NO 21
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ctgctgctgc tgc                                                          13

<210> SEQ ID NO 22
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gctgctcgtg ctg                                                          13

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gctgctgctg ctgctgctg                                                    19

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
cagacaauga uucacacttt t                                                 21

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      HTT TSS Forward sequence

<400> SEQUENCE: 25
ggttctgctt ttacctgcgg                                                   20

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Synthetic
      HTT TSS Reverse sequence

<400> SEQUENCE: 26

```
ctcgggccga ctcgc                                                      15
```

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence: Synthetic
      Exon 1, Forward sequence

<400> SEQUENCE: 27

```
ggtccaagat ggacggc                                                    17
```

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      Exon 1, Reverse sequence

<400> SEQUENCE: 28

```
agcaccgggg caatgaat                                                   18
```

<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence: Synthetic
      5' of CAG repeat, Forward sequence

<400> SEQUENCE: 29

```
attgccccgg tgctgag                                                    17
```

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      5' of CAG repeat, Reverse sequence

<400> SEQUENCE: 30

```
ggacttgagg gactcgaagg                                                 20
```

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      Gene body (intron 1), Forward sequence

<400> SEQUENCE: 31

```
gctccctcac ttgggtcttc                                                 20
```

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      Gene body (intron 1), Reverse sequence

<400> SEQUENCE: 32

```
caagttctcg ccccaactct                                                 20
```

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      Gene body (intron 1), Forward sequence

<400> SEQUENCE: 33
gtcaggcttg ccagaatacg                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      Gene body (intron 1), Reverse sequence

<400> SEQUENCE: 34
tggggttccg ctagatgttt                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      Gene body (intron 1), Forward sequence

<400> SEQUENCE: 35
gaagaccttt ctgctgggct                                              20

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      Gene body (intron 1), Reverse sequence

<400> SEQUENCE: 36
tctcctttgt caaggcagca a                                            21

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      Gene body (intron 1), Forward sequence

<400> SEQUENCE: 37
ttcctatctg gtgtttccct gac                                          23

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      Gene body (intron 1), Reverse sequence

<400> SEQUENCE: 38
ttaacactcg attaaccctg aca                                          23

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      Gene body (intron 1), Forward sequence

<400> SEQUENCE: 39
tgagtaaaga cctcaagcga gt                                              22

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      Gene body (intron 1), Reverse sequence

<400> SEQUENCE: 40
gaagattttg gacctgttcc ccc                                             23

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      Exon 30, Forward sequence

<400> SEQUENCE: 41
tggggacagt acttcaacgc                                                 20

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      Exon 30, Reverse sequence

<400> SEQUENCE: 42
accttgaaaa tgtttcttct ggca                                            24

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      Exon 67, Forward sequence

<400> SEQUENCE: 43
tcatcagcag gatgggcaag                                                 20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      Exon 67, Reverse sequence

<400> SEQUENCE: 44
agtcagcagc cggtgatatg                                                 20

```
<210> SEQ ID NO 45
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(600)
<223> OTHER INFORMATION: This sequence may encompass 3-200 "cag"
      repeating units
<220> FEATURE:
<223> OTHER INFORMATION: See specification as filed for detailed
      description of substitutions and preferred embodiments

<400> SEQUENCE: 45
cagcagcagc agcagcagca gcagcagcag cagcagcagc agcagcagca gcagcagcag      60
cagcagcagc agcagcagca gcagcagcag cagcagcagc agcagcagca gcagcagcag     120
cagcagcagc agcagcagca gcagcagcag cagcagcagc agcagcagca gcagcagcag     180
cagcagcagc agcagcagca gcagcagcag cagcagcagc agcagcagca gcagcagcag     240
cagcagcagc agcagcagca gcagcagcag cagcagcagc agcagcagca gcagcagcag     300
cagcagcagc agcagcagca gcagcagcag cagcagcagc agcagcagca gcagcagcag     360
cagcagcagc agcagcagca gcagcagcag cagcagcagc agcagcagca gcagcagcag     420
cagcagcagc agcagcagca gcagcagcag cagcagcagc agcagcagca gcagcagcag     480
cagcagcagc agcagcagca gcagcagcag cagcagcagc agcagcagca gcagcagcag     540
cagcagcagc agcagcagca gcagcagcag cagcagcagc agcagcagca gcagcagcag     600

<210> SEQ ID NO 46
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(600)
<223> OTHER INFORMATION: This sequence may encompass 3-200 "cag"
      repeating units
<220> FEATURE:
<223> OTHER INFORMATION: See specification as filed for detailed
      description of substitutions and preferred embodiments

<400> SEQUENCE: 46
cagcagcagc agcagcagca gcagcagcag cagcagcagc agcagcagca gcagcagcag      60
cagcagcagc agcagcagca gcagcagcag cagcagcagc agcagcagca gcagcagcag     120
cagcagcagc agcagcagca gcagcagcag cagcagcagc agcagcagca gcagcagcag     180
cagcagcagc agcagcagca gcagcagcag cagcagcagc agcagcagca gcagcagcag     240
cagcagcagc agcagcagca gcagcagcag cagcagcagc agcagcagca gcagcagcag     300
cagcagcagc agcagcagca gcagcagcag cagcagcagc agcagcagca gcagcagcag     360
cagcagcagc agcagcagca gcagcagcag cagcagcagc agcagcagca gcagcagcag     420
cagcagcagc agcagcagca gcagcagcag cagcagcagc agcagcagca gcagcagcag     480
cagcagcagc agcagcagca gcagcagcag cagcagcagc agcagcagca gcagcagcag     540
cagcagcagc agcagcagca gcagcagcag cagcagcagc agcagcagca gcagcagcag     600

<210> SEQ ID NO 47
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gactcgaaca agcaagag                                                       18

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gcctttaaca aaaccttaat ttc                                                 23

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gagctattgt aatgaccagt c                                                   21

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tgaccaagga aagcaaag                                                       18

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51
gaagaatcag tccaggagac c                                                   21

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
tgccagtgtc aattatatct tccacaa                                             27

<210> SEQ ID NO 53
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
ccgugugaau cauugucuu                                                    19

<210> SEQ ID NO 54
<211> LENGTH: 216
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
cagcagcagc agcagcagca gcagcagcag cagcagcagc agcagcagca gcagcagcag      60
cagcagcagc agcagcagca gcagcagcag cagcagcagc agcagcagca gcagcagcag     120
cagcagcagc agcagcagca gcagcagcag cagcagcagc agcagcagca gcagcagcag     180
cagcagcagc agcagcagca gcagcagcag cagcag                               216

<210> SEQ ID NO 55
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
cagcagcagc agcagcagca gcagcagcag cagcagcagc agcag                      45
```

The invention claimed is:

1. One or more anti-gene oligonucleotides adapted to hybridize to DNA in an HTT gene, which are based on locked nucleic acids, phosphorodiamidate morpholino oligomers (PMO) or equivalent oligonucleotide analogues comprising a (CAG)$_n$ sequence, and whose target is a sequence where the majority of the repeats are CAG/CTG, and where the first complete repeat is optionally preceded by a G/G or an AG/TG, and/or where the last repeat is optionally followed by a C/C or a CA/CT, wherein n is between 3 and 200, for use in treatment and/or prevention of Huntington's disease, or for use in diagnosis of Huntington's disease and where the anti-gene oligonucleotides target non-canonical DNA structures, including hairpin and cruciform.

2. One or more anti-gene oligonucleotides according to claim 1, for use in prevention of Huntington's disease, where prevention is related to blocking the CAG/CTG repeat expansion.

3. One or more anti-gene oligonucleotides according to claim 1, for use in down regulating the expression of an HTT gene.

4. One or more anti-gene oligonucleotides according to claim 1, for use in down regulating HTT mRNA and protein levels in afflicted subjects.

5. One or more anti-gene oligonucleotides according to claim 1, in combination with other Huntington's disease therapy, selected from the group comprising siRNAs, splice-switching oligonucleotides, single nucleotide polymorphism (SNP) targeting oligonucleotides, zinc finger nucleases and antisense oligonucleotides working via either RNase-mediated degradation or steric blocking of the HTT mRNA.

6. One or more anti-gene oligonucleotides according to claim 1, wherein n is 12, 13, 14, 15, 16, 18 or 19.

7. One or more anti-gene oligonucleotides according to claim 1, wherein the oligonucleotides comprise a phosphodiester (PO) or a phosphorothioate (PS) backbone.

8. One or more anti-gene oligonucleotides according to claim 1, wherein the oligonucleotide is based on locked nucleic acids, phosphorodiamidate morpholino oligomers, lipid-modified forms of LNA or related oligonucleotide analogues selected from the group comprising 2',4'-constrained oligonucleotides and oligonucleotides with modifications in their 2' or 5 positions.

9. One or more anti-gene oligonucleotides according to claim 8, wherein the oligonucleotides are selected from one or more of ethyl bicyclic nucleic acids, 2'-O-methyl, 2'-aminoglycyl, piperazino-modified 2'-aminonucleotides and 5-propargylamino-LNA, aminated 2'-amino-LNA nucleotides.

10. One or more anti-gene oligonucleotides according to claim 1, wherein the oligonucleotides are selected from the group comprising 2'-O-methyl RNA/LNA, and 2'-glycylamino 5-methylcytosine LNA.

11. One or more anti-gene oligonucleotides according to claim 10, wherein the oligonucleotides are selected from the group comprising CAG-14PS-OMe (2'-O-methyl) and CAG-14PS-gly (2'-aminoglycyl).

12. One or more anti-gene oligonucleotides according to claim 1, wherein the oligonucleotides are based on 2'-aminoglycyl modified nucleotide, such as modified A, G, C or T.

13. One or more anti-gene oligonucleotides according to claim 1, wherein the oligonucleotides are selected from the group comprising CAG-10PS, CAG-12PS and CAG-12PO, CAG-13PS and CAG-13PO, CAG-14PS and CAG-14PO, CAG-14PS-OMe, CAG-14PS-gly, CAG-15PS, CAG-16PS, CAG-18PS and CAG-19PS.

14. A delivery system for administration of one or more oligonucleotides, comprising
   a) one or more of oligonucleotides adapted to hybridize to DNA in an HTT gene, which are based on locked nucleic acids, phosphorodiamidate morpholino oligomers (PMO) or equivalent oligonucleotide analogues comprising a $(CAG)_n$ sequence, and whose target is a sequence where the majority of the repeats are CAG/CTG, and where the first complete repeat is optionally preceded by a G/G or an AG/TG, and/or where the last repeat is optionally followed by a C/C or a CA/CT, and wherein n is between 3 and 200,
   b) a liquid in which the one or more of oligonucleotides are dissolved, and optionally
   c) a cell penetrating peptide/protein, such as PepFect 14 (PF14), or
   d) a cationic lipid, or
   e) a nuclear localization signal peptide, or
   f) an aptamer facilitating targeting and uptake, optionally together with a pharmaceutically acceptable carrier, adjuvant and/or excipient.

15. A delivery system according to claim 14, comprising a cell penetrating peptide/protein, such as PepFect 14 (PF14, optionally together with a pharmaceutically acceptable carrier, adjuvant and/or excipient, wherein the one or more of oligonucleotides comprise a phosphodiester (PO) backbone.

16. A combination of any one or more of the oligonucleotides according to claim 1, together with other Huntington's disease therapies, such as siRNAs, splice-switching oligonucleotides, single nucleotide polymorphism (SNP) targeting oligonucleotides, zinc finger nucleases and antisense oligonucleotides working via either RNase-mediated degradation or steric blocking of the HTT mRNA.

17. The delivery system according to claim 14 for use in down regulating the expression of a HTT gene, or in targeting non-canonical DNA structures at the CAG/CTG repeat sequence, including hairpin and cruciform, or for use in down regulating HTT mRNA and protein levels in afflicted subjects, or in diagnosis treatment and/or prevention of HD in afflicted subjects or subjects at risk of being afflicted.

18. A method for diagnosis of Huntington's disease, whereby the method comprises the steps of
   1) isolating genomic DNA from a biological sample, and optionally cleaving the isolated DNA,
   2) adding any one or more anti-gene oligonucleotides adapted to hybridize to DNA in an HTT gene, which are based on locked nucleic acids, phosphorodiamidate morpholino oligomers (PMO) or equivalent oligonucleotide analogues comprising a $(CAG)_n$ sequence, and whose target is a sequence where the majority of the repeats are CAG/CTG, and where the first complete repeat is optionally preceded by a G/G or an AG/TG, and/or where the last repeat is optionally followed by a C/C or a CA/CT, and wherein n is between 3 and 200, and
   3) determining length and sequence and/or number of CAG/CTG repeats in the HTT gene.

19. The method according to claim 18, whereby cleaving is done using DNA restriction enzymes, CRISPR-Cas9 based DNA cleavage or by fragmentation using ultra sonication.

* * * * *